United States Patent
Jeon et al.

(10) Patent No.: US 9,442,069 B2
(45) Date of Patent: Sep. 13, 2016

(54) APPARATUS FOR IN-VITRO IMAGING AND ANALYSIS OF DENTAL SAMPLES

(71) Applicant: QUANTUM DENTAL TECHNOLOGIES INC., Toronto (CA)

(72) Inventors: Jinseok Jeon, Windsor (CA); Koneswaran Sivagurunathan, Scarborough (CA); Stephen Abrams, Toronto (CA); Andreas Mandelis, Scarborough (CA); Joshua D. Silvertown, Toronto (CA); Bonny Wong, Markham (CA); Adam Hellen, Richmond Hill (CA)

(73) Assignee: QUANTUM DENTAL TECHNOLOGIES INC., Toronto, On (CA)

( * ) Notice: Subject to any disclaimer, the term of this patent is extended or adjusted under 35 U.S.C. 154(b) by 0 days.

(21) Appl. No.: 14/654,353

(22) PCT Filed: Mar. 14, 2013

(86) PCT No.: PCT/CA2013/050200
§ 371 (c)(1),
(2) Date: Jun. 19, 2015

(87) PCT Pub. No.: WO2014/094142
PCT Pub. Date: Jun. 26, 2014

(65) Prior Publication Data
US 2015/0346095 A1 Dec. 3, 2015

Related U.S. Application Data

(60) Provisional application No. 61/745,286, filed on Dec. 21, 2012.

(51) Int. Cl.
*F21V 9/16* (2006.01)
*G01N 21/63* (2006.01)
(Continued)

(52) U.S. Cl.
CPC .............. *G01N 21/63* (2013.01); *G01N 21/64* (2013.01); *G01N 33/4833* (2013.01); *G01N 2021/646* (2013.01); *G01N 2201/02* (2013.01); *G01N 2201/06113* (2013.01)

(58) Field of Classification Search
CPC .......... G01N 2021/646; G01N 21/63; G01N 21/64; G01N 2201/02; G01N 2201/06113; G01N 33/4833
USPC ....................................................... 250/458.1
See application file for complete search history.

(56) References Cited

U.S. PATENT DOCUMENTS

| | | | |
|---|---|---|---|
| 5,306,144 A | 4/1994 | Hibst et al. | |
| 6,584,341 B1 * | 6/2003 | Mandelis ............. | A61B 5/0088 433/29 |

(Continued)

OTHER PUBLICATIONS

R. J. Jeon et al., "Diagnosis of Pit and Fissure Caries using Frequency Domain Infrared Photothermal Radiometry and Modulated Laser Luminescence" Caries Research 38,497-513 (2004).

(Continued)

*Primary Examiner* — David J Makiya
*Assistant Examiner* — Taeho Jo
(74) *Attorney, Agent, or Firm* — Lynn C. Schumacher; Stephen W. Leonard; Hill & Schumacher

(57) ABSTRACT

A detection system is provided for the measurement of in-vitro dental samples. The detection system includes an optical detection module that is configured for the detection of optical signals that are emitted in response to the absorption of an incident optical beam, and a control and processing unit that is configured for processing the detected optical signals and generating an image. The system also includes a sample holder may be removed and subsequently replaced without requiring recalibration of the system. In some embodiments, the optical detection module is configured for combined measurement of photothermal radiation and luminescence in response to the absorption of the incident optical beam.

22 Claims, 28 Drawing Sheets

(51) Int. Cl.
*G01N 33/483* (2006.01)
*G01N 21/64* (2006.01)

(56) References Cited

U.S. PATENT DOCUMENTS

| | | | |
|---|---|---|---|
| 8,306,608 B2 | 11/2012 | Mandelis et al. | |
| 9,220,415 B2* | 12/2015 | Mandelis | A61B 5/0095 |
| 2002/0158211 A1* | 10/2002 | Gillispie | G01N 21/6408 250/458.1 |
| 2003/0058456 A1* | 3/2003 | Bodenmiller | G01B 11/2522 356/603 |
| 2004/0032594 A1* | 2/2004 | Weber | A61C 13/0004 356/601 |
| 2006/0032433 A1* | 2/2006 | Sakata | G01N 23/207 117/89 |
| 2006/0090361 A1* | 5/2006 | Matsuda | G01B 11/24 33/503 |
| 2007/0021670 A1* | 1/2007 | Mandelis | A61B 5/0088 600/473 |
| 2007/0041877 A1* | 2/2007 | Maurer | G01N 21/0332 422/400 |
| 2007/0081201 A1* | 4/2007 | Mcmurtry et al. | A61C 13/0004 358/494 |
| 2007/0134615 A1* | 6/2007 | Lovely | A61B 5/0088 433/29 |
| 2008/0081311 A1* | 4/2008 | Doumoto | A61C 13/12 433/50 |
| 2009/0079993 A1* | 3/2009 | Yatagai | A61B 5/0062 356/497 |
| 2009/0310146 A1* | 12/2009 | Pfeiffer | G06T 7/0028 356/615 |
| 2009/0324451 A1* | 12/2009 | Yin | B01L 9/523 422/400 |
| 2010/0019170 A1* | 1/2010 | Hart | A61B 1/043 250/459.1 |
| 2010/0288944 A1* | 11/2010 | Avdeef | G01N 21/0332 250/461.1 |
| 2011/0036360 A1* | 2/2011 | Lang | A61B 6/505 128/898 |
| 2011/0176147 A1* | 7/2011 | Marcil | G01B 11/25 356/602 |
| 2011/0287387 A1* | 11/2011 | Chen | A61C 9/006 433/215 |
| 2013/0141558 A1 | 6/2013 | Jeon et al. | |

OTHER PUBLICATIONS

A. Mandelis et al., "Novel Dental Depth Profilometric Imaging Using Simultaneous Frequency-Domain Infrared Photothermal Radiometry and Laser Luminescence", Biomedical Optoacoustics, Proc SPIE, A. Oraevsky (ed), 3916, 130-137 (2000).

L. Nicolaides et al., "Novel Dental Dynamic Depth Profilometric Imaging Using Simultaneous Frequency-Domain Infrared Photothermal Radiometry and Laser Luminescence", J Biomed Opt, 5, 31-39 (2000).

International Search Report in PCT/CA2013/050200 dated Sep. 5, 2013.

Written Opinion in PCT/CA2013/050200 dated Sep. 5, 2013.

* cited by examiner

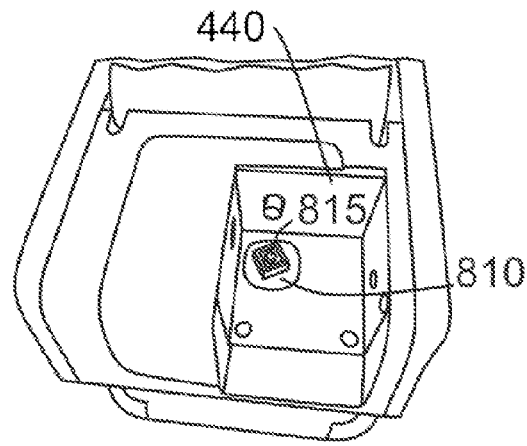
Figure 7(a)
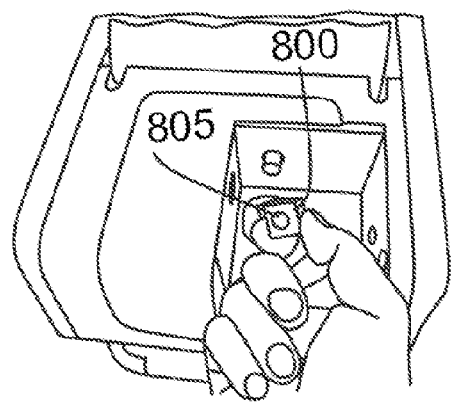
Figure 7(b)
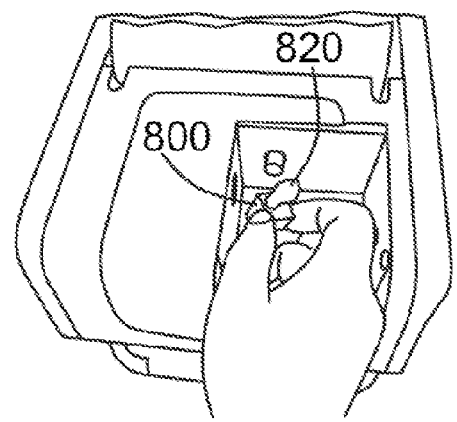
Figure 7(c)
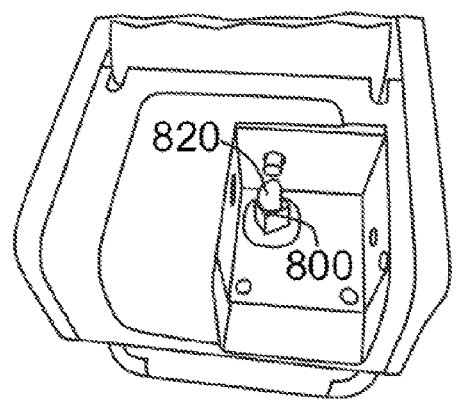
Figure 7(d)
Figure 7

| Camera Image of sample | The Canary Image | Canary Number | Canary Lab Image- Contrast Enhancement | Canary Lab Image- Contrast Enhancement with Camera Image |

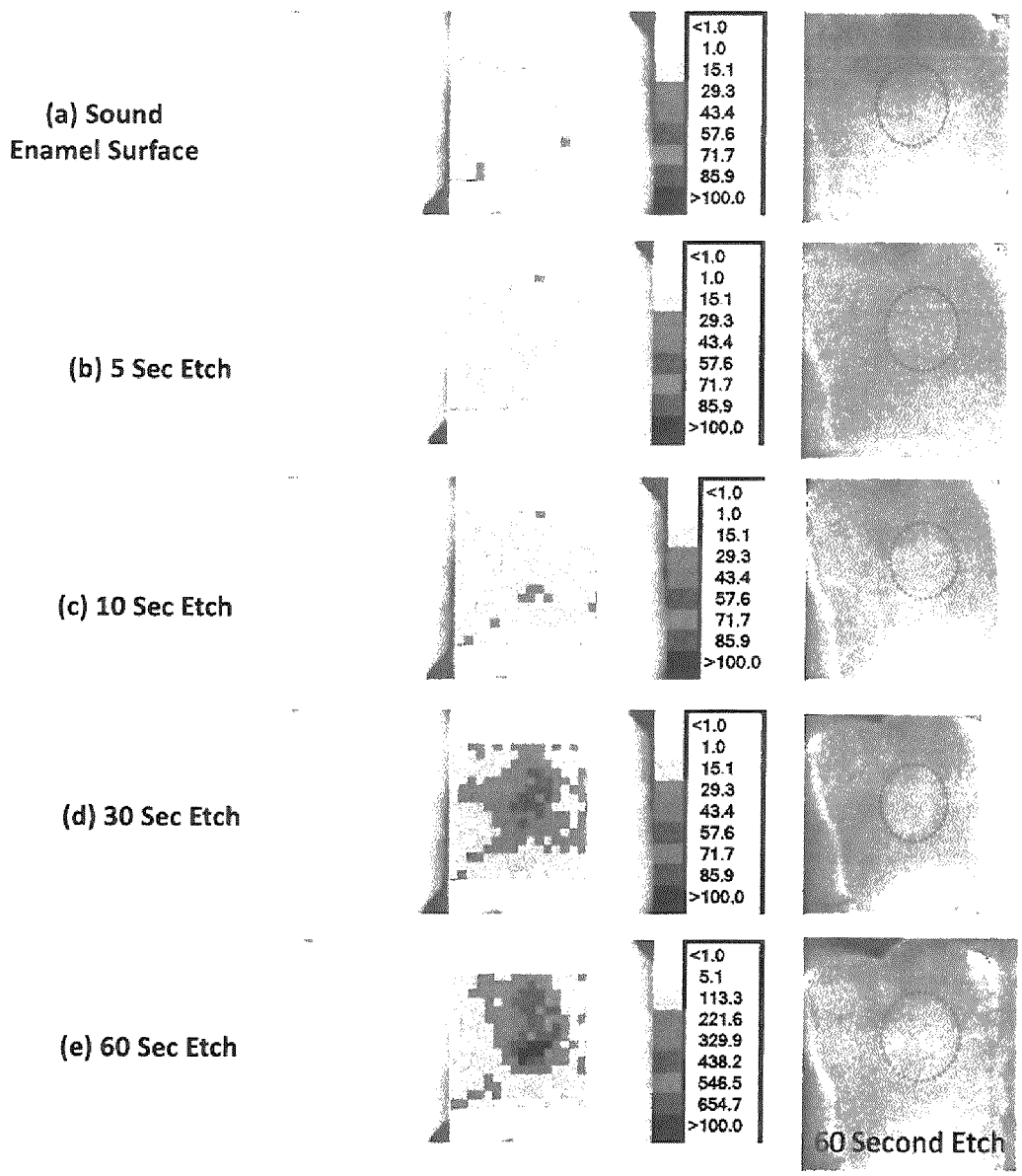
Figures 17(a)-(e)

APPARATUS FOR IN-VITRO IMAGING AND ANALYSIS OF DENTAL SAMPLES

CROSS-REFERENCE TO RELATED APPLICATION

This application is a National Phase application claiming the benefit of the international PCT Patent Application No. PCT/CA2013/050200, filed on Mar. 14, 2013, in English, which claims priority to U.S. Provisional Application No. 61/745,286, titled "APPARATUS FOR IN-VITRO IMAGING AND ANALYSIS OF DENTAL SAMPLES" and filed on Dec. 21, 2012, the entire contents of which are incorporated herein by reference.

BACKGROUND

The present disclosure relates to dentistry and oral health care.

With the widespread use of fluoride, the prevalence of dental caries has been considerably reduced. Nonetheless, the development of a non-invasive, non-contact technique that can detect and monitor early demineralization and or carious lesions on or beneath the enamel, dentin, root surface or dental restorations, is essential for the clinical management of this problem. A number of different diagnostic devices and methods have been developed to meet this need, including laser-induced fluorescence of enamel or to the fluorescence caused by porphyrins present in carious tissue [R. Hibst, K. Konig, "Device for Detecting Dental Caries", U.S. Pat. No. 5,306,144 (1994)] and photothermal radiometry [A. Mandelis, L. Nicolaides, C. Feng, and S. H. Abrams, "Novel Dental Depth Profilometric Imaging Using Simultaneous Frequency-Domain Infrared Photothermal Radiometry and Laser Luminescence", Biomedical Optoacoustics. Proc SPIE, A. Oraevsky (ed), 3916, 130-137 (2000), L. Nicolaides, A. Mandelis, and S. H. Abrams, "Novel Dental Dynamic Depth Profilometric Imaging Using Simultaneous Frequency-Domain Infrared Photothermal Radiometry and Laser Luminescence", J Biomed Opt, 5, 31-39 (2000), and R. J. Jeon C. Han A. Mandelis V. Sanchez S. H. Abrams "Diagnosis of Pit and Fissure Caries using Frequency Domain Infrared Photothermal Radiometry and Modulated Laser Luminescence" Caries Research 38,497-513 (2004)].

While the aforementioned methods and devices are general adapted for clinical use, other systems have been developed for in-vitro analysis of dental samples. Unfortunately, such systems generally are destructive in nature, and require the dental sample to be histologically cut. Such systems also lack sensitivity for determining the onset of dental defects and pathologies.

SUMMARY

A detection system is provided for the measurement of in-vitro dental samples. The detection system includes an optical detection module that is configured for the detection of optical signals that are emitted in response to the absorption of an incident optical beam, and a control and processing unit that is configured for processing the detected optical signals and generating an image. The system also includes a sample holder that may be removed and subsequently replaced without requiring recalibration of the system. In some embodiments, the optical detection module is configured for combined measurement of photothermal radiation and luminescence in response to the absorption of the incident optical beam.

Accordingly, in one aspect, there is provided a system for performing in-vitro measurements on a dental sample, the system comprising:

a housing;

an optical detection module provided within said housing, wherein said optical detection module is configured to direct an incident optical beam over a measurement region and to detect optical radiation responsively emitted by the dental sample when at least a portion of the dental sample is positioned at or near the measurement region;

a control and processing unit provided within said housing, wherein said control and processing unit is configured to control said optical detection module and to generate an image by processing signals provided by said optical detection module in response to the detection of the optical radiation;

a sample holder for supporting the dental sample; and an attachment mechanism provided within said housing for removably securing said sample holder in a preselected position and orientation relative to the measurement region;

wherein said attachment mechanism and said sample holder are configured such that said sample holder can be removed from the system and subsequently secured by said attachment mechanism without requiring recalibration of a relative position and orientation between the dental sample and the measurement region.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 7(a)-(d) are images showing the removable insertion of an example dental sample holder within the sample chamber of the system.

FIG. 11(b) shows the amplitude and phase components of the Canary Lab images with (with and without contrast enhancement).

FIG. 11(b) shows the amplitude and phase components of the Canary Lab images with (with and without contrast enhancement).

FIGS. 17(a)-(e) show Canary Lab images of a sequential etching experiment at various time points.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "diagnostic" refers to the measurement of a property of a sample. It is to be understood that this term is not intended to be limited to measurements for use in clinical diagnosis, and can instead refer to any type of measurement.

Figure 1A:
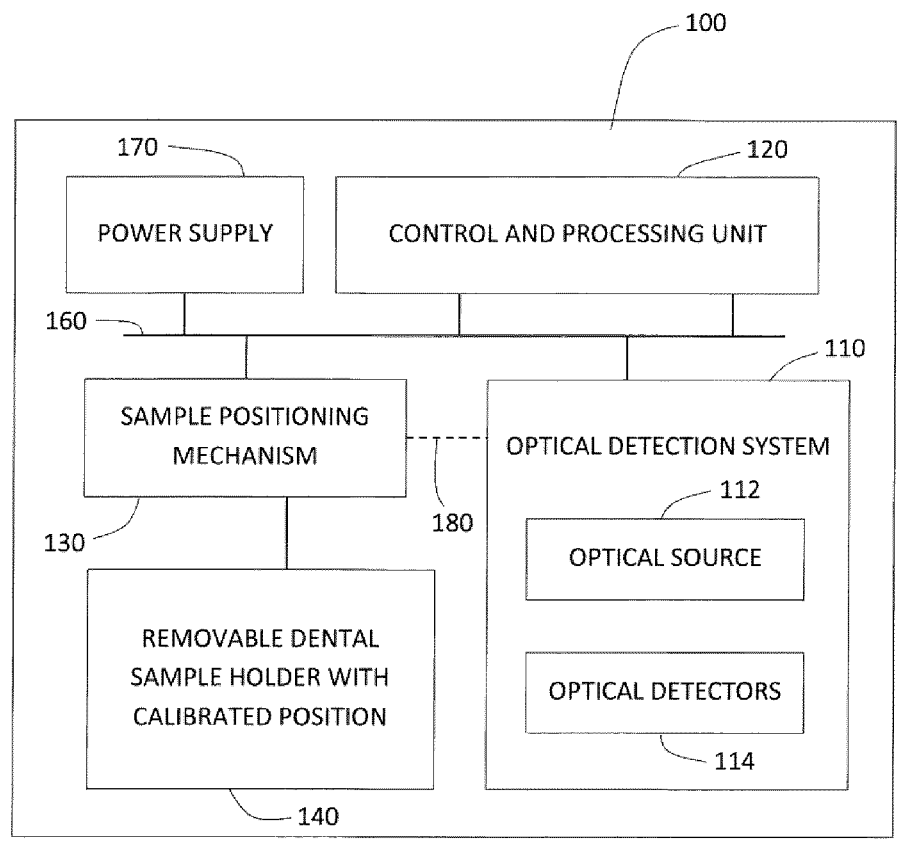
FIG. 1(a) is a block diagram of an example system for performing in-vitro analysis of dental samples.

Referring now to FIG. 1(a), an example system 100 for performing in-vitro analysis of dental samples is illustrated. Apparatus 100 includes optical detection system 110, control and processing unit 120, sample positioning mechanism 130, removable dental sample holder 140, and power supply 170.

Optical detection system 110 directs an incident optical beam from optical source 112 onto a dental sample supported by sample holder 140, and detects, with one or more optical detectors 114, radiation responsively emitted from the dental sample.

Control and processing unit 120 is interfaced, through bus 160, with optical detection system 110 for controlling optical source 112 and for receiving signals detected by optical detectors 114. Control and processing unit 120 is also interfaced with sample positioning mechanism 130, for controlling sample position of an incident optical beam relative to the sample and aligned photon detectors.

In one example implementation, optical detection system 110 may be a fluorescence and/or luminescence detection system. In another example implementation, described in detail below, optical detection system 110 may direct an incident optical beam onto the dental sample and the one or more detectors 114 may be adapted to detect photothermal radiation and/or luminescence that is emitted from the sample upon absorption of the incident optical radiation. In such an embodiment, a combination of laser photothermal radiometry and modulated luminescence may be employed to detect, assess, and monitor dental caries.

Figure 1B:
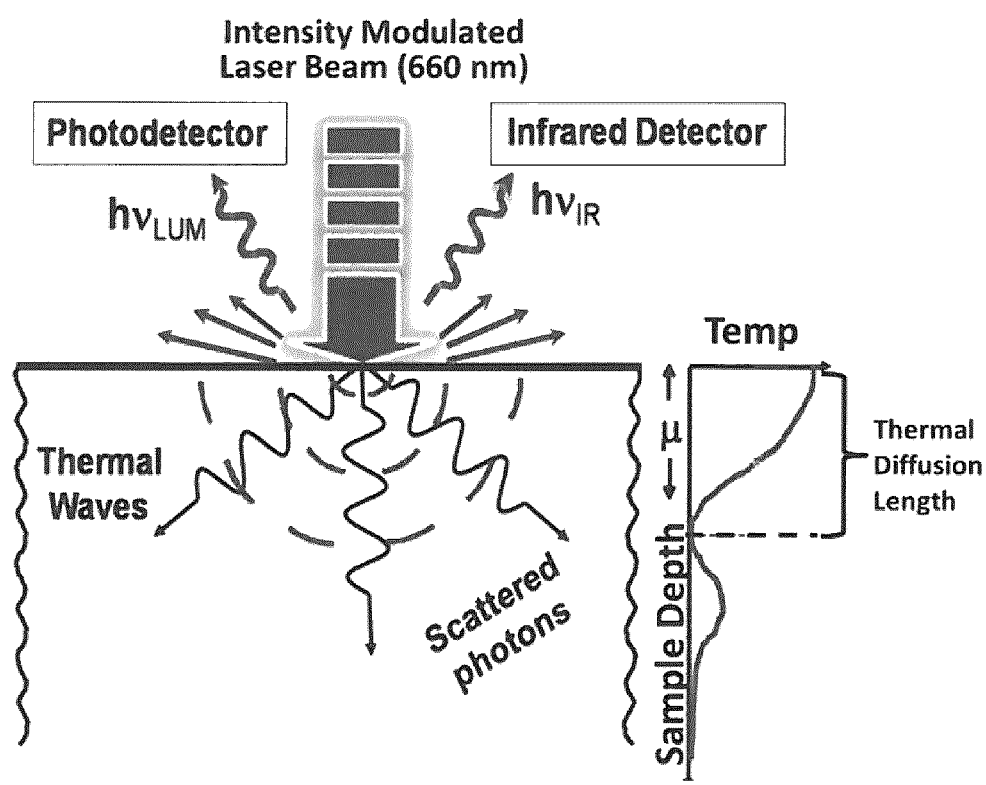
FIG. 1(b) illustrates the process of photothermal radiation and luminescence generation in a dental sample.

Photothermal radiation and luminescence technology is suitable for detecting and/or monitoring changes in smooth surface caries, pit and fissure caries, interproximal caries, root surface caries and erosive lesions. Using pulses of laser light focused on a tooth, the tooth emits fluorescence (or luminescence), and glows due to heat production, as shown in FIG. 1(b). The emitted radiation (mid-infrared) may be detected and processed to obtain information about the tooth's condition. For example, early mineral loss from a tooth causes small changes in the ultrastructure creating a more porous, less dense, environment. This affects the location, rate and transport of the generated heat and fluorescence throughout the sample.

Figure 1C:
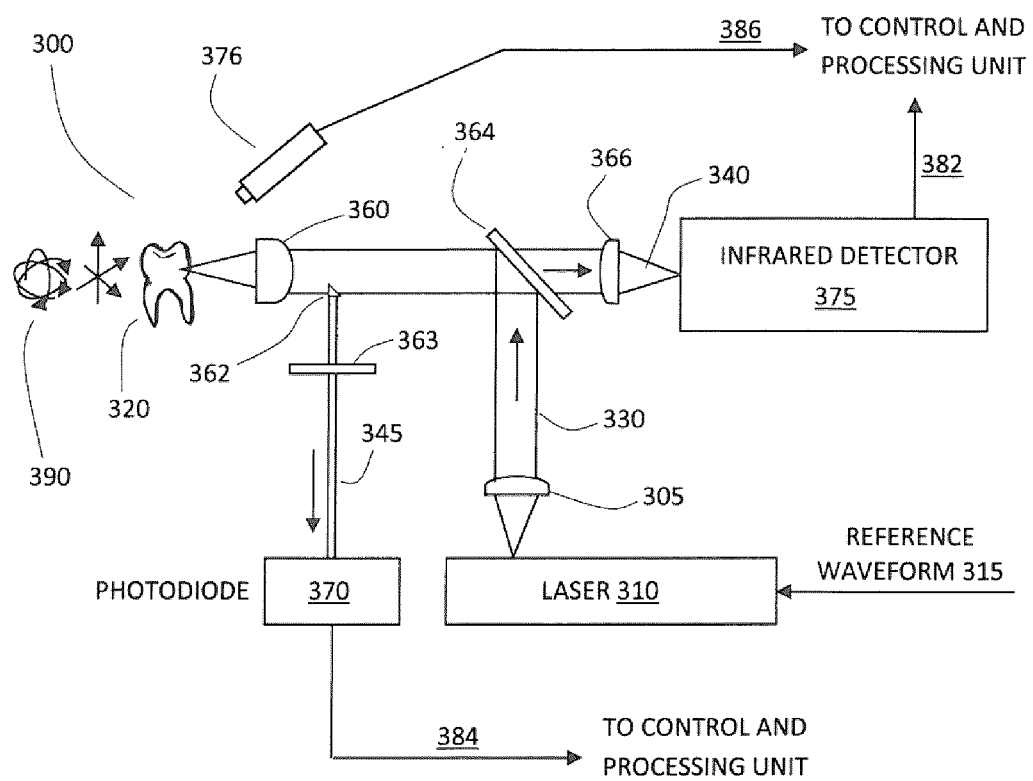
FIG. 1(c) illustrates a non-limiting example implementation of an in-vitro system in which the optical detection system is a photothermal radiation and luminescence detection system.

FIG. 1(c) illustrates a non-limiting example in which optical detection system 110 is a photothermal radiation and luminescence detection system, where the Figure shows the main components of such a device. Further details are disclosed in United States Patent Publication No. US20070021670, published on Jan. 25, 2007, which is incorporated herein in its entirety by reference. U.S. Pat. No. 6,584,341, issued to Mandelis et al. entitled "Method and apparatus for detection of defects in teeth", which is incorporated herein in its entirety by reference, discloses a similar system. Such a photothermal and luminescence detection system, as disclosed in these two US patent documents, may be used for scanning and data capture of dental tissue.

As shown in FIG. 1(c), example photothermal radiation and luminescence collinear detection system 300 includes laser light source 310 for irradiating a portion of a dental sample 320 with an incident optical beam 330 having a wavelength (or plurality of wavelengths) that are absorbed by dental sample 320. Incident optical beam 330 is collimated by a collimating lens(es) 305, reflected by dichroic or high-pass filter 364 (such as a properly coated germanium window), and focused onto dental sample 320 via focusing and collection lens 360. Incident optical beam 330 is modulated via reference waveform 315, which is provided by control and processing unit 120. Reference waveform modulates the laser beam directly, for example, via an external optical chopper, or directly modulated, for example, via modulating the laser driving current in the case of a semiconductor laser. Other modulation methods and mechanisms may alternatively be employed.

Modulated photothermal radiation and modulated luminescence are responsively emitted from dental sample 320 upon absorption of incident optical beam 330. Modulated photothermal radiation and luminescence are collected by focusing and collection lens 360. A portion of the collected modulated luminescence is split off using beam pick-off mirror or prism 362 and optically filtered with filter 363 to form modulated luminescence beam 345, which is detected via photodetector 370. Collected modulated photothermal radiation is transmitted through dichroic or high-pass filter 364 and focused onto infrared detector 375 by focusing lens 366. Camera 376 may be included to provide an image of the dental sample. Modulated photothermal radiometric signals 382, modulated luminescence signals 384, and camera output 386 are sent to control and processing unit 120 for processing.

In one example implementation, laser light source 310 may a laser diode having a wavelength of approximately 660 nm, an output laser power of approximately 130 mW at maximum DC current, and the laser power may be controlled such that the incident power on the sample is less than approximately 50 mW, focused to an effective spot size of approximately 50±10 µm, with a modulation frequency of approximately 2 Hz. The slower laser modulation frequency of approximately 2 Hz may assist an investigator in monitoring changes in the dental sample from the tooth surface down to 5 mm below the tooth surface.

In another example implementation, the incident optical beam 330 and the collected modulated photothermal radiation and modulated luminescence may be delivered in a common fiber optic bundle, which is bifurcated such that individual fibers, or collections of fiber, are appropriately routed to the laser source 310, infrared detector 375, and photodetector 370. For example, a first optical fiber may have a proximal end in optical communication with the laser and a distal end in optical communication with the focusing and collection lens 360, probe head for transmitting light from the light source a first pre-selected number of multi-mode optical fibers are near-infrared-transmitting optical fibers for transmitting the modulated luminescence signals to the photodiode detector 370, and a second pre-selected number of the multi-mode optical fibers are mid-infrared-transmitting optical fibers for transmitting the modulated photothermal radiometry signals to the infrared detector 375. Such a fiber bundle implementation is described in further detail in US Patent Application Publication No. US20070021670.

In the present example implementation involving the detection of modulated photothermal radiation and modulated luminescence, processing and control unit 120 includes a phase-sensitive detection system for demodulating the emitted modulated photothermal signals into photothermal phase and amplitude components and the modulated luminescence signals into luminescence phase and amplitude signals, and may also include a waveform generator for providing a reference waveform for modulating incident optical beam 330. In such an embodiment, the laser intensity is modulated at a desired frequency and both the detector signal and a reference signal related to the phase of the modulated laser current is provided to the lock-in amplifier. It will be apparent to those skilled in the art that other modulation methods may be used. The lock-in amplifier may be provided on a data acquisition board housed within control and processing unit 120. An example of suitable data acquisition board for providing lock-in functionality is the National Instruments NI USB-6221-OEM board. Alternatively, the lock-in amplified may be provided separately in an additional system that is interfaced to the control and processing unit.

Processing and control unit 120 may also be programmed to compare the detected photothermal phase and amplitude signals to reference photothermal phase and amplitude signals (such as signals pertaining to a reference sample) and to compare the detected luminescence phase and amplitude signals to reference luminescence phase and amplitude signals (again, such as signals pertaining to a reference sample) to determine differences, if any, between the dental sample and the reference values and optionally correlating any differences with the presence of defects and/or pathologies in the dental sample.

Figure 1D:
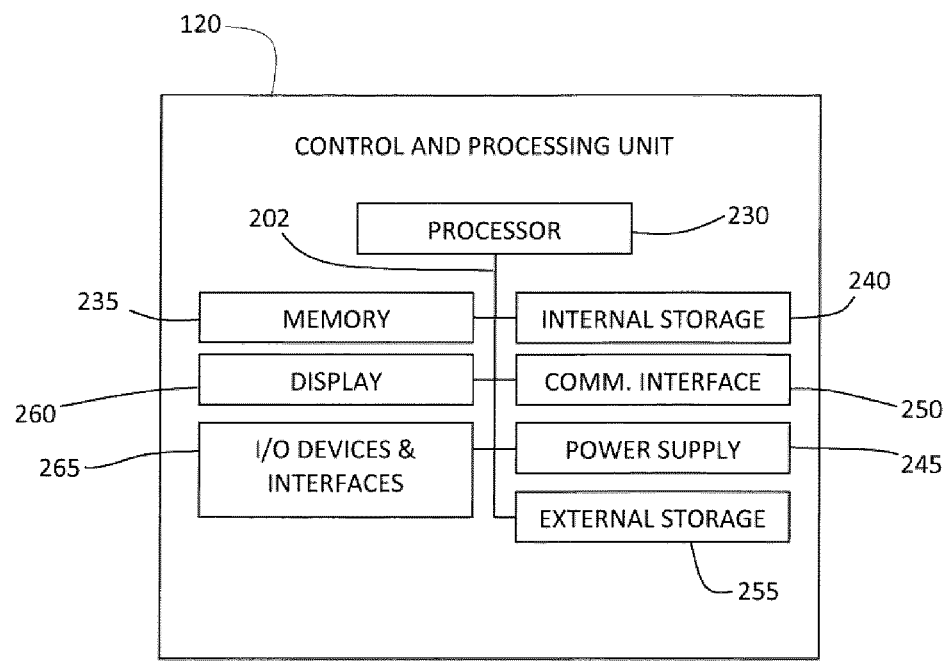
FIG. 1(d) illustrates an example implementation of a control and processing unit.

FIG. 1(d) illustrates an example implementation of control and processing unit 120, which may include one or more processors 230 (for example, a CPU/microprocessor), bus 202, memory 235, which may include random access memory (RAM) and/or read only memory (ROM), one or more internal storage devices 240 (e.g. a hard disk drive, compact disk drive or internal flash memory), a power supply 245, one more communications interfaces 250, external storage 255, a display 260 and various input/output devices and/or interfaces 265 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, and/or a microphone for capturing speech commands).

Control and processing unit 120 may be programmed with a set of instructions which when executed in the processor causes the system to perform one or more methods described in the disclosure. Control and processing unit 120 may include many more or less components than those shown. For example, as noted above, processing and control unit 120 may include a phase-sensitive detection system, such as a software-based lock-in amplifier, and a waveform generator for producing the reference waveform.

Although only one of each component is illustrated in FIG. 1(d), any number of each component can be included control and processing unit 120. For example, a computer typically contains a number of different data storage media. Furthermore, although bus 202 is depicted as a single connection between all of the components, it will be appreciated that the bus 202 may represent one or more circuits, devices or communication channels which link two or more of the components. For example, in personal computers, bus 202 often includes or is a motherboard.

In one embodiment, control and processing unit 120 may be, or include, a general purpose computer or any other hardware equivalents. Control and processing unit 120 may also be implemented as one or more physical devices that are coupled to processor 120 through one of more communications channels or interfaces. For example, control and processing unit 120, or a portion thereof, can be implemented using application specific integrated circuits (ASIC). Alternatively, control and processing unit 120 can be implemented as a combination of hardware and software, where the software is loaded into the processor from the memory or over a network connection.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Referring again to FIG. 1(a) and FIG. 1(c), system 100 may also include a scanning/positioning mechanism 130 for varying the position and/or orientation of incident optical beam 330 relative to dental sample 320. In one example embodiment, the position and orientation of dental sample is fixed and incident optical beam 330 is scanned over a selected region on the dental sample. For example, a scanning mechanism may employ a combination of one or more scanning mirrors (controlled via a galvanometer) and a suitable scanning lens, such as a flat-field, f-theta, or telecentric lens.

In another embodiment, the dental sample may be translated and/or reoriented relative to a stationary incident optical beam, as shown in FIG. 1(c) at 390. An example implementation of such an embodiment is described in further detail below.

In another embodiment, one or more of the detectors may be an imaging detector (for example, an array of pixels) and the incident beam may be focused onto on area suitable for imaging with the imaging detector. Examples of suitable imaging detectors are described in United States Patent Publication No. US20070021670. The dental sample may also be translated and/or reoriented relative to the imaging beam in order to image different areas of a given sample.

Figure 1E:
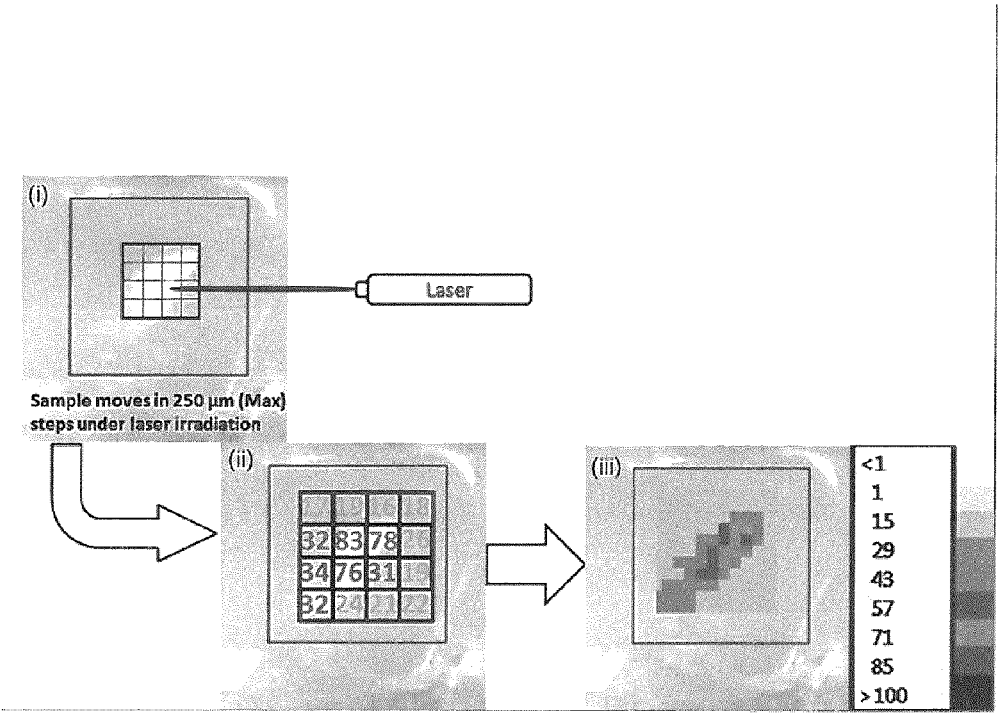
FIG. 1(e) illustrates the scanning process and the formation of an image.

FIG. 1(e) illustrates an example process of scanning a dental sample to obtain an image. In step (i), the incident optical beam is scanned relative to the dental sample across a grid having a pre-selected pixel resolution. In step (ii), the measured signal for each pixel is recorded and optionally processed to obtain a numerical quantity (for example, amplitude and phase information may be combined to form a single measure, and/or data from two or more modalities may be combined to form a single measure). In step (iii), the numerical values associated with each pixel are combined to form an image that may be displayed to the operator via a user interface.

Figure 1F:
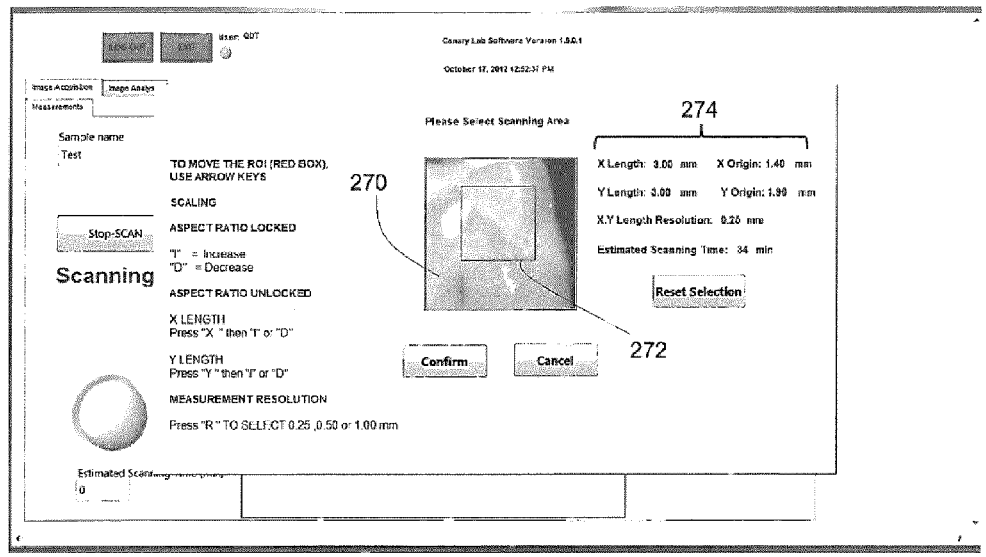
FIGS. 1(f)-1(h) are screenshots of a user interface for image acquisition and image processing.
Figure 1G:
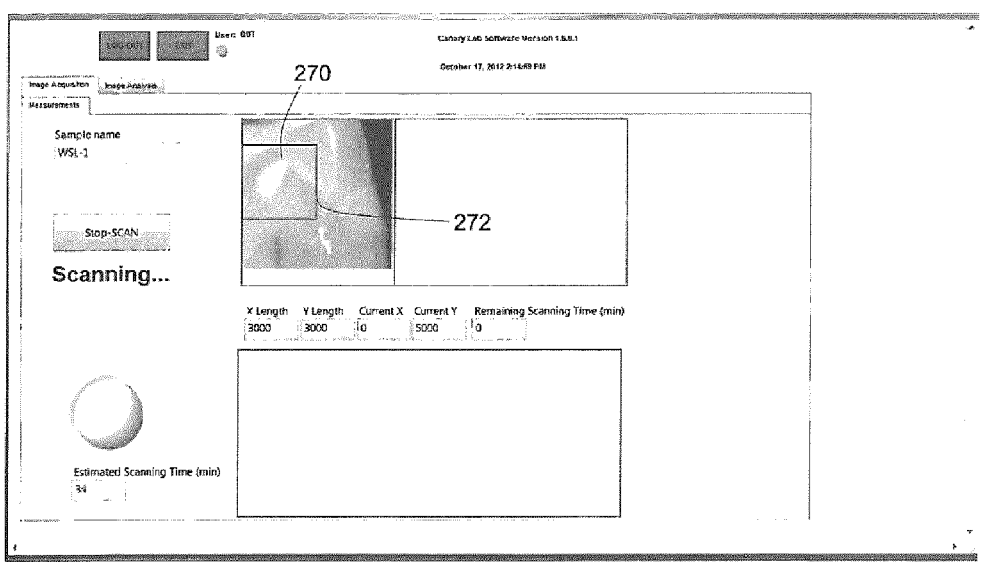
Figure 1H:
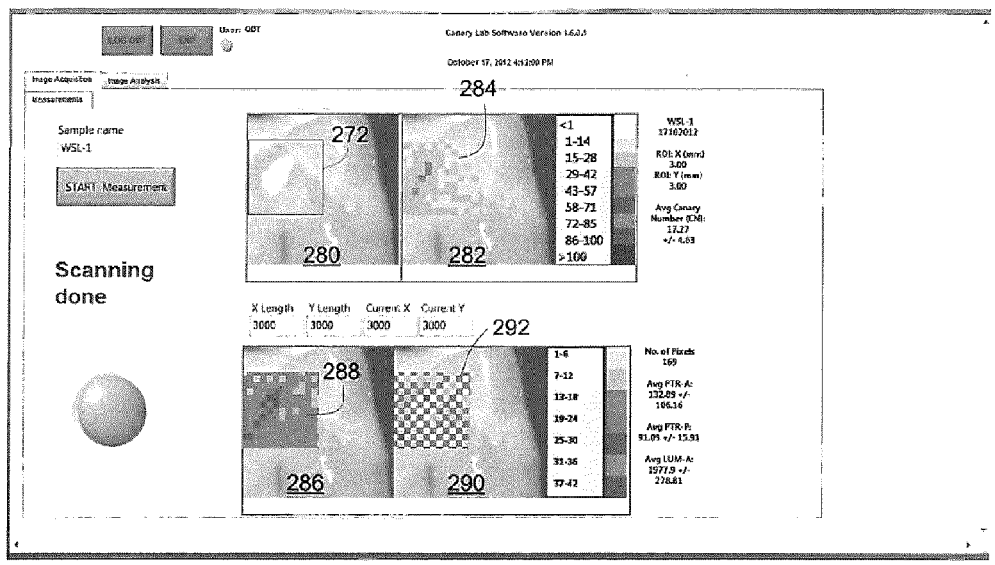

FIGS. 1(f)-1(h) show screen shots of an example user interface for measuring and processing images obtained from system 300. FIG. 1(f) shows a user interface screen for defining the scanning area. A camera image 270 of the dental sample, obtained by camera 376, is displayed, and the operator is instructed to select a desired scanning area. In the present example, the scanning area is defined by the relative positioning of scanning area box 272 relative to camera image 270. The operator may also select the spatial scanning resolution to be used during the scanning process.

The scanning area is definable relative to the camera image due to knowledge of the relative positioning between camera 376 and incident optical beam 330. Due to the spatial registration (e.g. by a fixed mechanical relationship) of these two modalities, is scanned relative to the dental sample. This known spatial relationship between the imaging camera and the incident optical beam also allows for image registration between the camera image and the measured image that is obtained from the radiation detected in response to the incident optical beam.

FIG. 1(g) shows an example user interface screen that may be presented to the operator during the scanning of the sample, after a suitable scanning area has been selected. Scanning parameters, such as the current scanning position, total scanning area, and remaining scanning time, may be presented to the operator during the scanning process.

FIG. 1(h) is an example user interface screen for displaying the results of a scan. The example user interface screen shows four image renderings, each providing the operator with different information. Image 280 shows the camera image with rectangle 272 denoting the area scanned during image acquisition. Image 284 shows the camera image co-registered with the measured image 284. In the present non-limiting example, the measured image is an image associated with the photothermal and luminescence signals produced in response to the incident optical beam. The numerical scale plots the "Canary Number", a parameter described in detail in Example 1 below.

Image 286 includes the camera image, and a co-registered enhanced image 288, where the latter is obtained by processing the measured image to improve its image quality. In one embodiment enhanced image 288 is obtained by processing the data to improving image contrast. For example, the contrast enhancement of the image may be applied to reduce the range of values displayable in the image, in order to allow an investigator to examine the region of interest with greater accuracy and/or precision. For example, in one example implementation, the contrast enhanced image may be obtained by applying an autoscaling algorithm to the image 284, such that the contrast among the pixels with the greatest and least intensities are maximized.

In another example embodiment, the range of values displayed in the image may be selected by the operator. This embodiment enables the operator to select and investigate a specific feature in higher resolution. It is to be understood that these image processing steps may be employed by a processor or computing device interfaced with the system, such as processor 230 of control and processing unit 120, as shown in FIG. 1(*d*).

Image 290 of FIG. 1(*h*) shows another example image rendering embodiment, in which contrast enhanced image 288 is combined with the camera image to produce composite image 292. In composite image 292, checkered pixels are provided to allow the operator to view the camera image adjacent to every other pixel from the contrast enhanced image.

It is to be understood that the user interface screens shown herein, and the form of the rendered and registered images shown in the screens, are provided as example implementations only, and that the form and content of the user interface may vary without departing from the scope of the present disclosure.

Referring again to FIG. 1(*a*), system 100 is configured to support a dental sample holder 140, which may be removed from system 100. System 100 is includes a positioning and retention mechanism to allow for the removal and subsequent replacement of dental sample holder 140 in a predetermined position and orientation without requiring the recalibration of the incident optical beam relative to the dental sample. This allows for a wide range of in-vitro analyses and experimental protocols, such as, but not limited to, the ability to remove a sample, process the dental sample to modify the dental sample, and subsequently re-measure the dental sample, without having to re-calibrate the relative position and/or orientation of the dental sample relative to the incident optical beam.

There are a wide range of different mechanisms for positioning and removably retaining a dental sample holder within system 100, such that the dental sample holder is removable and replaceable without requiring recalibration. For example, system 100 may include, on a base or platform, one or more mechanically keyed features for receiving a dental sample holder in a pre-selected position and orientation. In some example implementations, a locking or retention mechanism may be employed to mechanically fix the position and orientation of the dental sample holder within system 100. Example locking or retention mechanisms include a spring-biased locking member, a magnet or electromagnet for removably attaching a magnetic dental sample holder, a ball detent mechanism, one or more fasteners such as a set screw, a friction fit mechanism, a vacuum fitting mechanism, or another suitable locking mechanism.

Figure 2A:
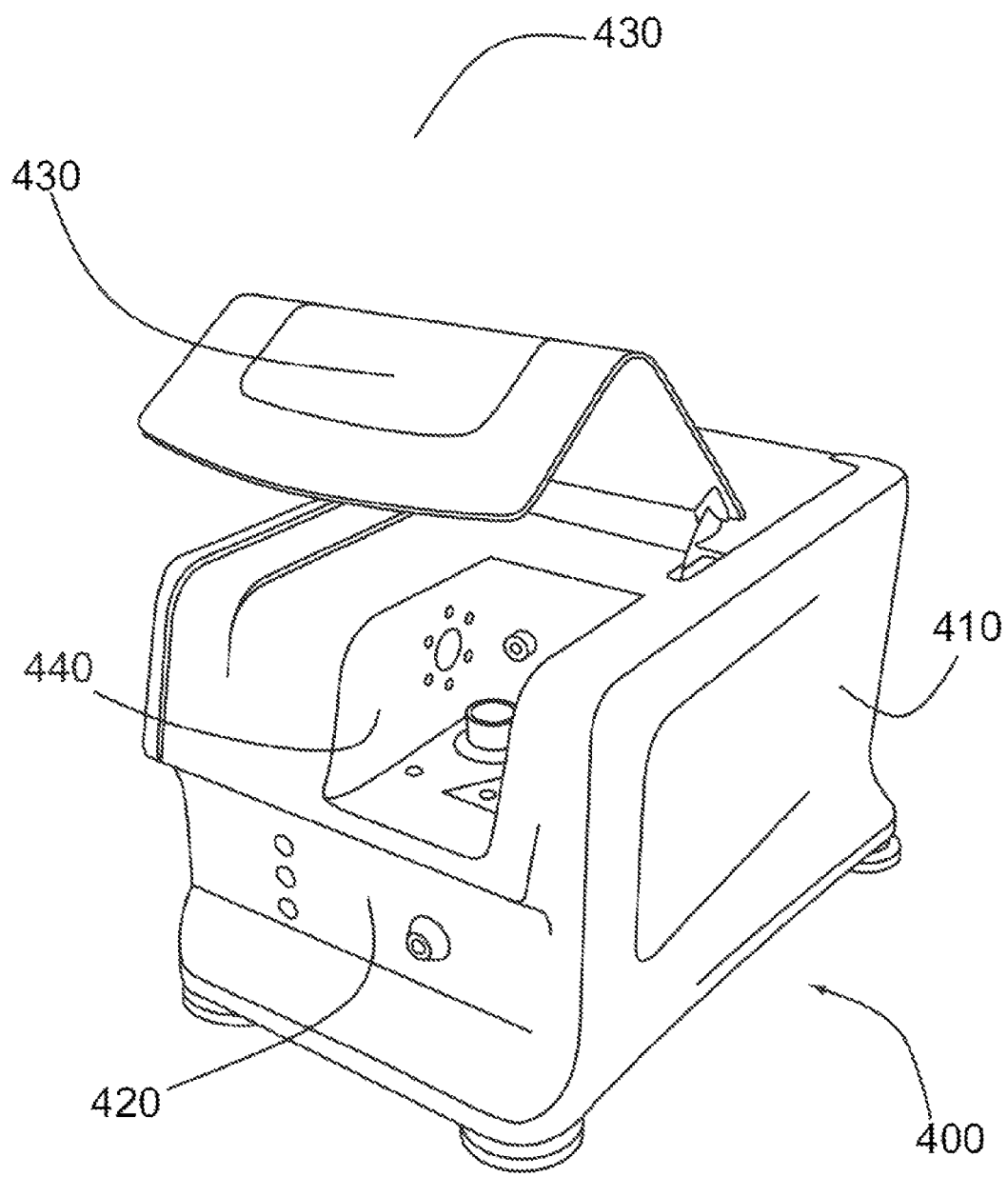
FIGS. 2(a)-(c) are images of an example implementation of an in-vitro detection system for optically scanning and imaging dental samples.
Figure 2B:
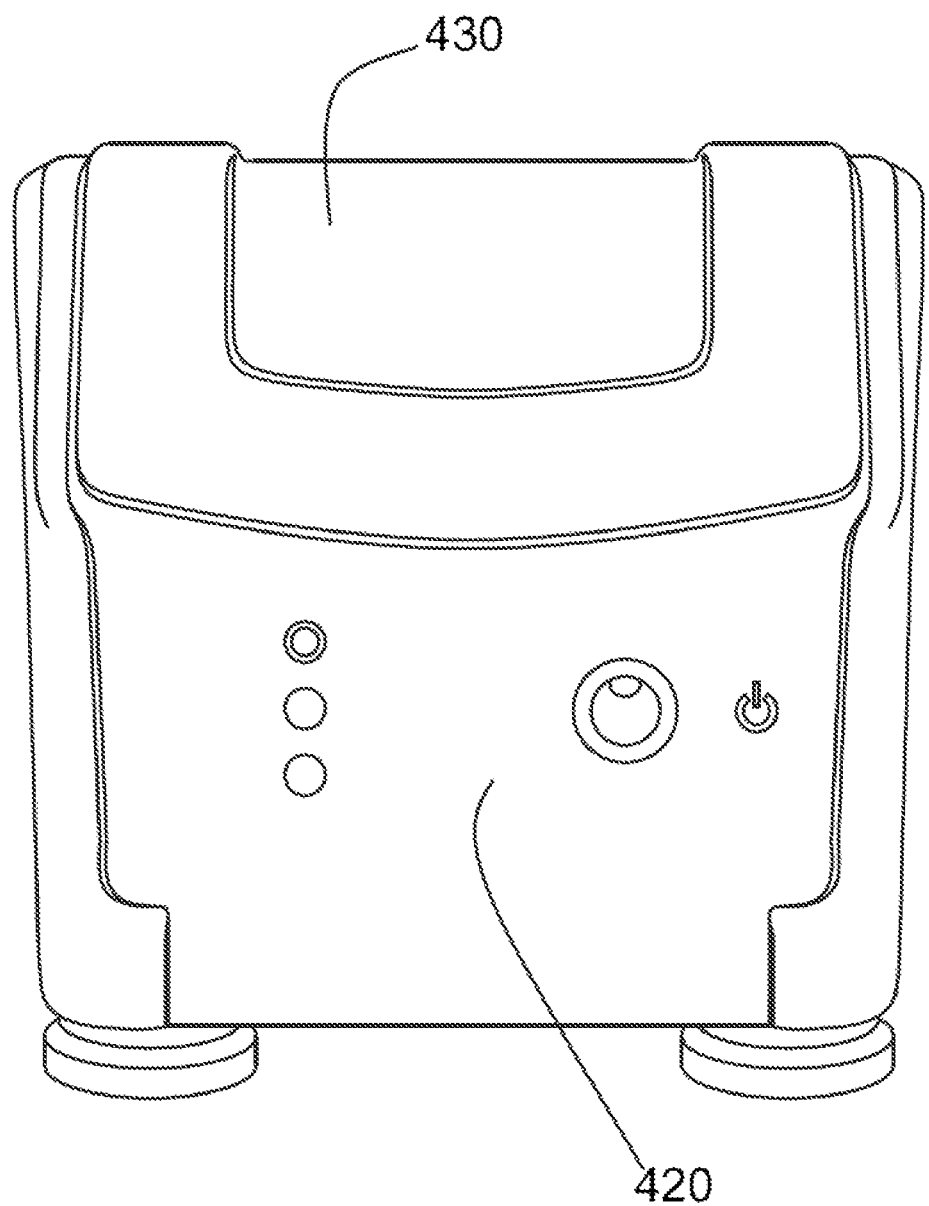
Figure 2C:
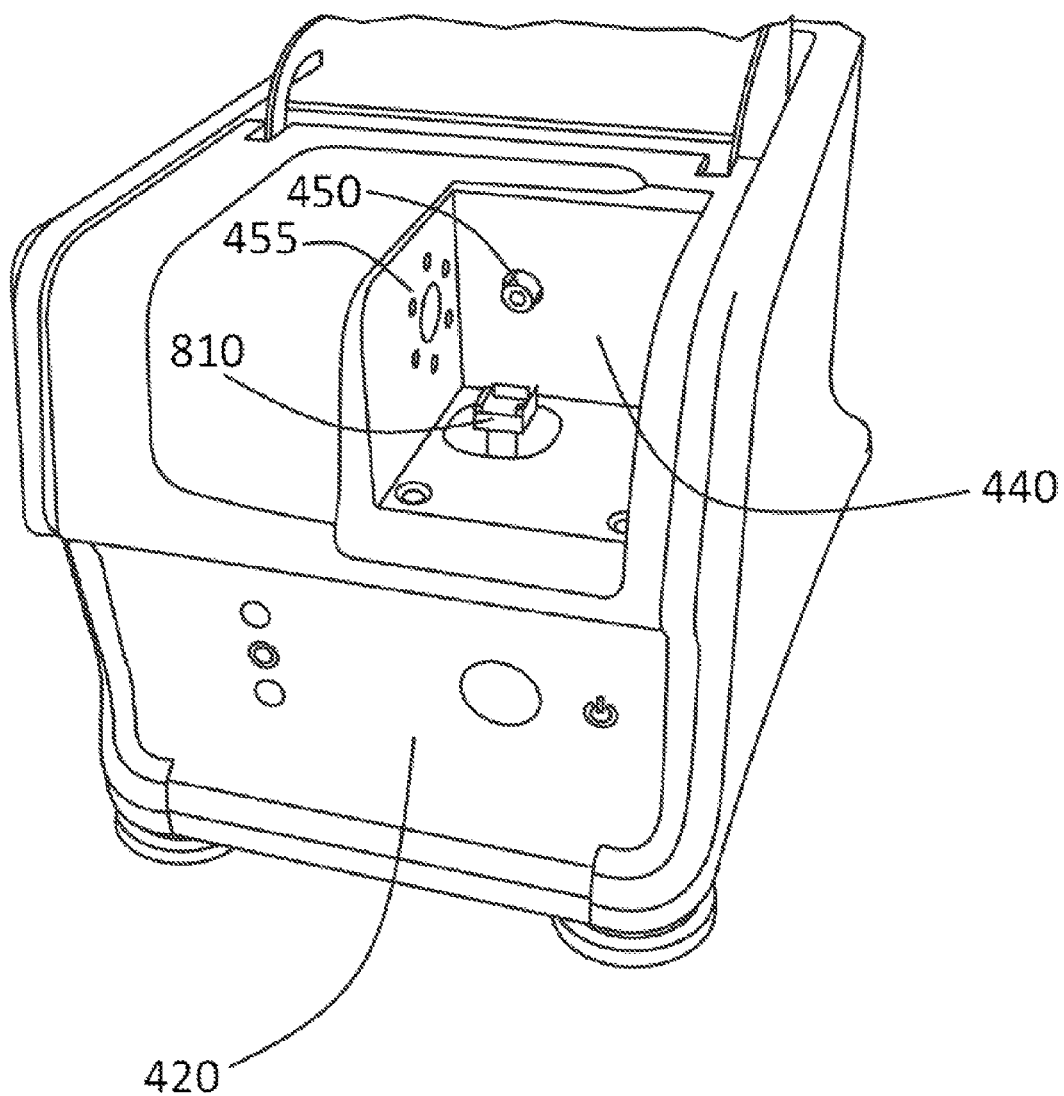

Referring now to FIGS. 2(*a*)-(*c*), an example implementation of an in-vitro detection system 400 for optically scanning dental samples is shown, where the example system has been configured for performing photothermal radiation and luminescence measurements on a dental sample. In the present example embodiment, the dental sample is mounted on a sample holder that can be magnetically retained in a fixed position, removed from system 400, and subsequently replaced without requiring calibration of the relative position between the dental sample holder and the incident optical beam, as described further below.

In some embodiments, the dental sample may be, for example, whole tooth samples, enamel sections, teeth containing composites, amalgam or other filling materials, teeth covered with a dental sealant, and teeth from different non-human species.

System 400 includes main instrument body 410, front indicator and/or control panel 420, door 430, and sample chamber 440. Door 430, when closed, encloses sample chamber 440 in order to prevent external background light from interfering with the measurement process. Door 440 also acts as a safety measure by preventing the incident optical beam from propagating outside of the system. In some embodiments, an interlock mechanism may be included, which turns off or blocks the output of the internal laser whenever door 440 is opened.

As shown in FIG. 2(*c*), sample chamber 440 includes a sample holder receiving base 810 for magnetically and removably securing a dental sample holder (described below) in a fixed position, focusing and collection lens assembly 450 for delivering the incident optical beam and collecting emitted photothermal radiation and luminescence, and optional imaging camera 455 for obtaining images of the dental sample during analysis. In one example implementation, imaging camera 455 obtains photographs depicting the location of the scan, and may be a standard VGA camera (having a resolution of 640×480 pixels), and may output the image in a format such as JPEG.

Figure 3:
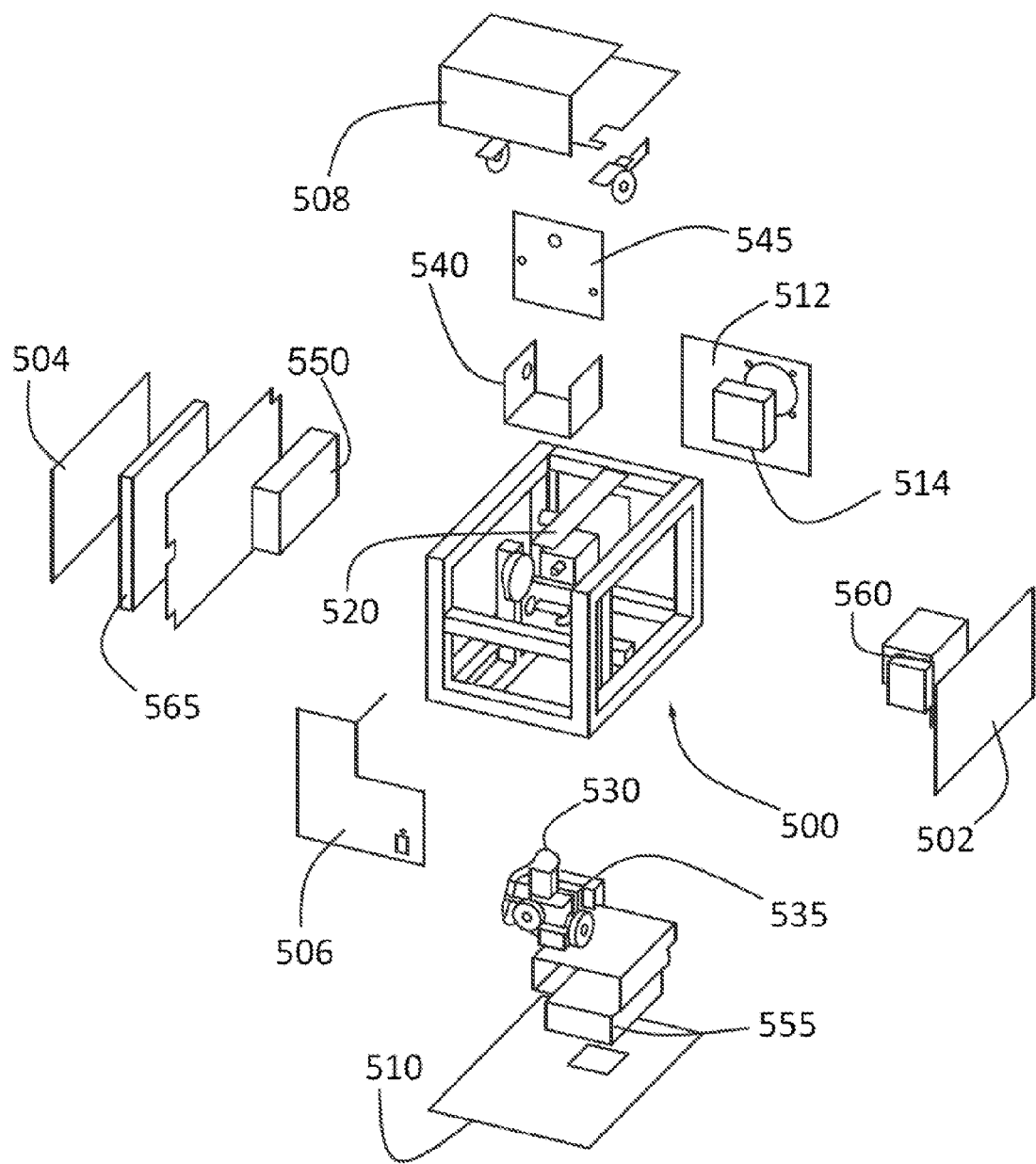
FIG. 3 is an assembly diagram showing several components of an in-vitro detection system for optically scanning dental samples.

FIG. 3 provides an assembly diagram showing several components of system 400. Chassis 500 mechanically supports the components of the system and provides an external frame, to which side panels 502 and 504, front panel 506, top panel 508, bottom panel 510, and rear panel 512 with fan 514, are assembled. Several internal optical components, including an optical block (described below), detectors, a camera, and a laser, are shown supported by chassis 500 at 520. System 400 also includes infrared detector power supply 550, USB hub 555, stepper motor driver 560, and data acquisition board 565. The sample holder receiving base (not shown) is supported by platform 530, which is translated and reoriented by position and orientation control assembly 535. The sample chamber is defined by lower and side wall portion 540, and back wall portion 545.

Figure 4:
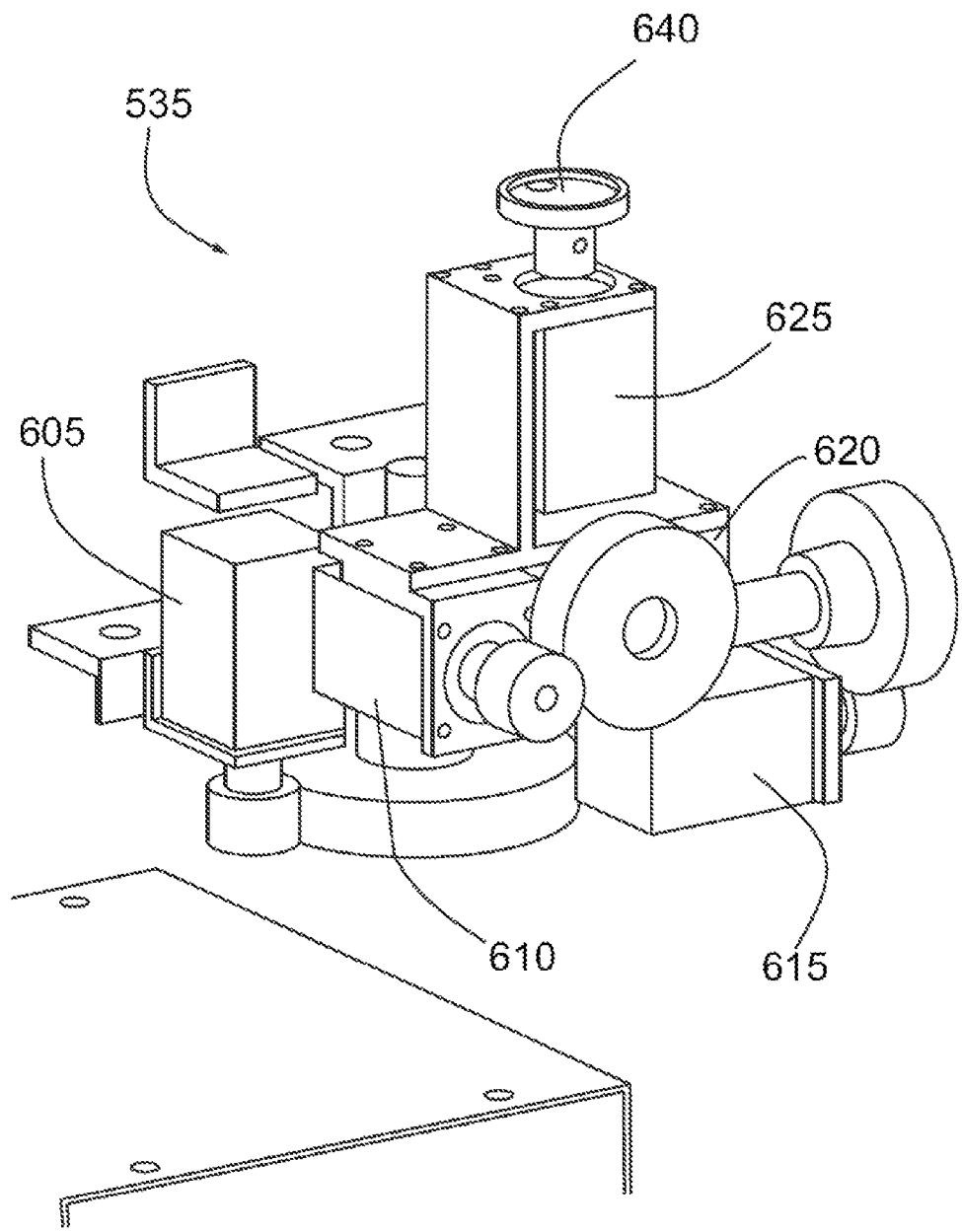
FIG. 4 illustrates an example embodiment of a position and orientation control assembly for achieving three-dimensional position and orientation control of a sample holder.

FIG. 4 illustrates an example embodiment of position and orientation control assembly 535 for achieving three-dimensional position and orientation control of a sample holder. 605, 615, 610 and 625 are stepper motors for Z, X, Focus, and rotational stages, respectively. 620 is a 2 axis translational stage.

In one example implementation, position and control assembly 535 may include a 360° rotational motorized stage (for example, with a 1.8° max. resolution), with a spatial scan capability suitable for measurements across a region of approximately 6 mm×6 mm, optionally with a motorized sample stage resolution of up to approximately 2 μm, with an optional default resolution of approximately 250 μm. In other embodiments, the resolution may be larger, such as 250, 500, or 1000 μm.

Figure 5A:
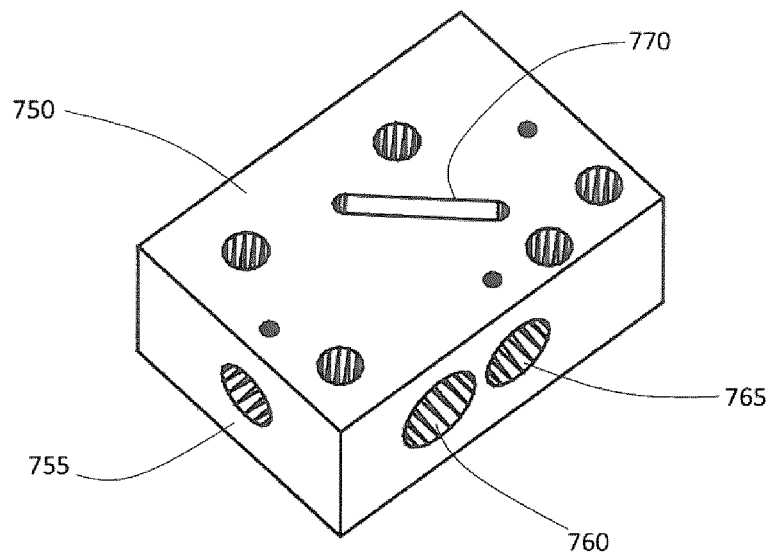
FIGS. 5(a) and 5(b) show illustrations of an example implementation of an optical block for housing several components of the optical detection system.
Figure 5B:
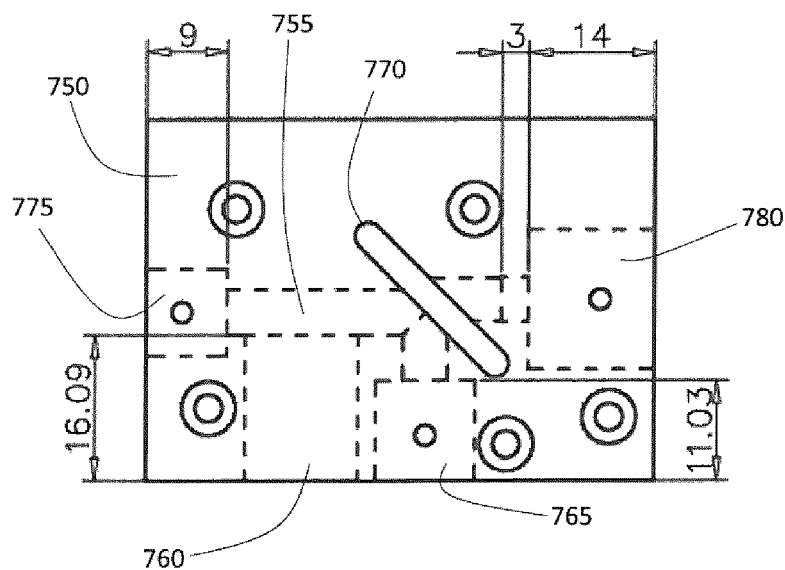
Figure 6:
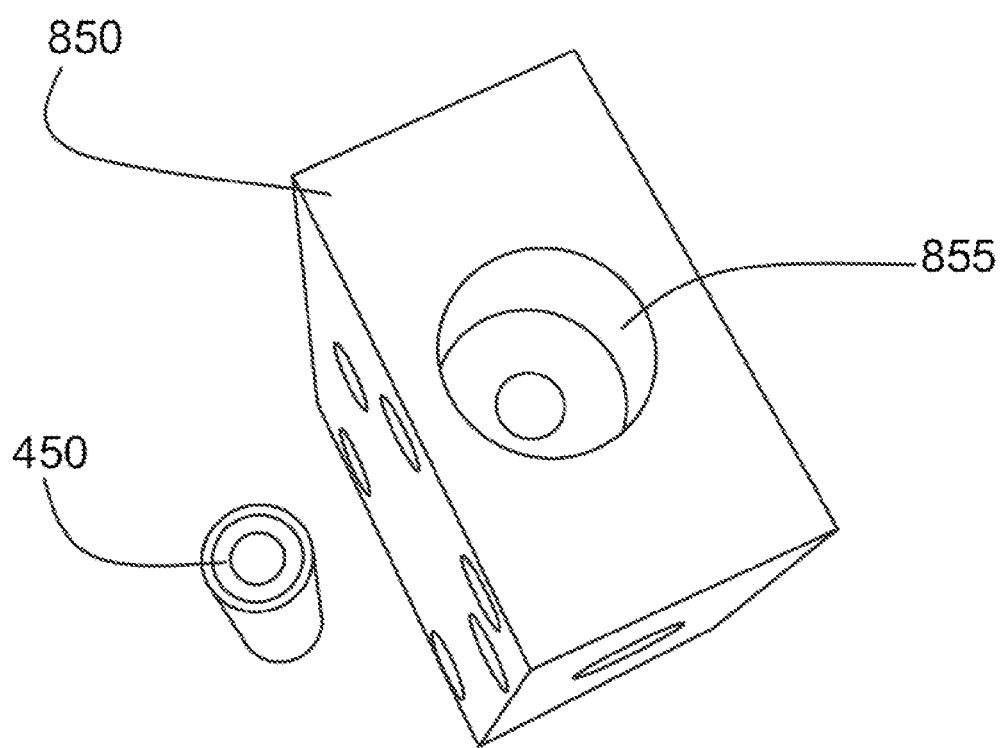
FIG. 6 is a photograph of an example optical block for housing several components of the optical detection system.
Figure 8:
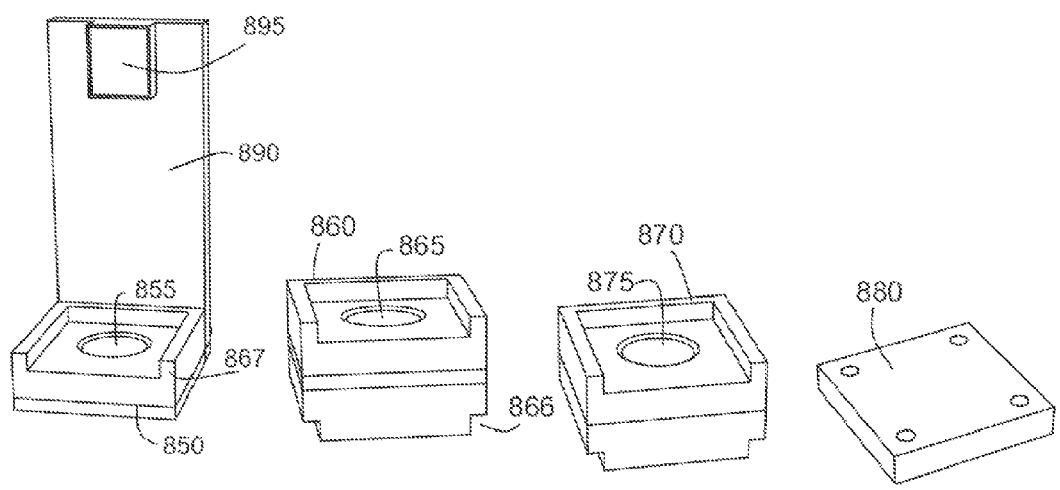
FIG. 8(a)-(d) are photographs of the components of an example sample holder.

FIGS. 5(*a*) and (*b*) and FIG. 6 show an example implementation of an optical block 750 for housing several components of the optical detection system, for implementing the optical configuration shown in FIG. 1(*c*). Optical block 750, which may be formed of a resilient and thermally conductive material such as aluminum, includes a plurality of channels and recesses for housing one or more of the optical components of the optical detection system. In the example embodiment shown in FIGS. 5(*a*) to (*b*) and FIG. 6, particularly in FIG. 5(*b*), optical block 750 includes a primary channel 755 for delivering the incident optical beam and the collected photothermal radiation and luminescence.

Recess 775 is formed to house focusing and collection lens assembly 450, as shown in FIG. 6. Recess 760 is provided to support a photodiode assembly (not shown) that includes a photodiode and appropriate beam sampling optics, such as a prism or mirror that intercepts a portion of the collected luminescence beam. Recess 765 is provided to accommodate a laser source, such as a semiconductor laser. Laser energy is deflected off of a dichroic or high-pass filter that is itself supported within slot 770. Recess 780 accommodates an infrared detector (or at least a portion thereof) for detecting the photothermal radiation that is transmitted through the dichroic or high-pass filter. Accordingly, it is apparent that optical block 750 is an implementation optical detection system 110 in which a plurality of the optical components are aligned and supported within a common optical bench, which provides mechanical stability among the plurality of optical components.

Referring now to FIGS. 7(a)-(d), a series of images are show in which dental sample holder 800 is placed onto base 810. In FIG. 7(a), sample chamber 440 is shown including base 810, which is connected (from below) to position and orientation control assembly 535 (located beneath sample chamber 440), such that the position and/or orientation of the dental sample holder may be varied when dental the sample holder is installed on base 810. Base 810 includes base magnet 815 for removably receiving and securing the dental sample holder.

In FIG. 7(b), a user is shown holding dental sample holder 800 in an inverted orientation, revealing sample holder magnet 805. Sample holder magnet 805 and base magnet 815 are oriented such that when dental sample holder 800 is contacted with base 810, sample holder is removably secured and in a fixed and predetermined orientation. Although not shown in the figure, base 810 and dental sample holder 800 may include one or more keyed features that are defined and arranged so that dental sample holder 800 may only be received onto base 810 in a specific orientation. The non-magnetic portions of dental sample holder 800 and base 810 may be formed from aluminum, or another suitable resilient material, which is non-magnetic. In other embodiments, base 810 and sample holder 800 may be formed from materials that are substantially or entirely magnetic in nature (including, but not limited to, ferromagnetic and electromagnetic materials).

FIG. 7(c) shows the user contacting dental sample holder 800 (which includes dental sample 820) with the base, such that base magnet and sample holder magnet apply a retaining force to secure dental sample holder 800 in place. Dental sample holder 800 is shown secured in place in FIG. 7(d).

FIGS. 8(a)-8(d) and 9(a)-9(h) illustrate an example embodiment for positioning a dental sample 820 on the dental sample holder, and for accommodating various different sample heights. In this example embodiment, the dental sample holder is composed of one or more platforms (860, 870 and 880) that are magnetically connectable, and mountable to be magnetically secured in base 810, in a manner as described above.

FIGS. 8(a)-8(d) also show mounting platform 850 for positioning a dental sample at an appropriate height for scanning within the system. Sample platform 880, and one or more optional secondary platforms 860 and 870 (for example, having heights of 10 mm and 6.5 mm, respectively) may be stacked and magnetically retained onto optional mounting platform 850 while securing a dental sample to sample platform 880. Sample platform 880 includes a top surface for securing a dental sample (for example, using an adhesive such as epoxy, or a retention mechanical mechanism). In the embodiment shown, sample platform 880 also includes screw tap holes (e.g. 9 mm apart), which may be employed to fix a resin molded sample. Example lateral dimensions for sample platform 880 are 15×15 mm.

Magnetic retention between any two platforms is achieved by magnets embedded within the platforms, such as magnets 855, 865, and 875 in mounting platform and the two secondary platforms 860 and 870, respectively, and magnets in the underside of the platforms (not shown in FIGS. 8(a)-(d); alternatively, one or more magnets may extend through full thickness of the platform, so that only one magnet is needed). Keyed features, such as channels 866 and corresponding slots 867, may be included to further secure the platforms during assembly, and to ensure that the platforms can be attached in a selected configuration. It is to be understood that although two secondary platforms (860 and 870) are shown in FIG. 8, three or more secondary platforms may be optionally employed.

As shown in FIGS. 9(a)-9(h), mounting platform 850 may include a calibration marker or feature 895 that defined a reference location indicating the location of the measurement region (the area or region that is to be scanned and/or imaged by the system) relative to the bottom surface of the sample holder when the sample holder is installed on the base. In the example implementation shown, marker 895 may be a block or other physical marker having a front surface that approximately coincides with the focal plane (i.e. the object plane) of the scanned area. For example, marker 895 may have dimensions of approximately 6 mm×6 mm. In other embodiments, marker 895 may be a portion of a surface, where the portion of the surface is marked, for example, coloured, scribed, or otherwise modified, to show the scanning area. In one embodiment, marker 895 includes an indication, such as a cross hair or grid, that defines the center and the scanning area of the measurement region. One or more additional markers (for example, lateral markers on the sides of sample holder 800), may be included to indicate the depth of field or Rayleigh range of the optical scanning beam.

FIGS. 9(a)-(d) show four different stacking combinations for selecting a different height of the top surface of sample mounting platform 880 relative to mounting platform 850, in order to position dental sample 820 at an appropriate height relative to marker 895. In configuration (a), sample mounting platform 880 is directly, and magnetically, attached to mounting platform 850, while in configuration (d), both secondary platforms 860 and 870 are included in order to raise the height of sample platform 880 (as such, in the present embodiment, sample platform 880 and the one or more optional secondary platforms together constitute the sample holder).

Accordingly, when mounting a dental sample, sample mounting platform 880, and, optionally, one or more secondary platforms (e.g. 860 and 870), are placed on mounting platform 850 in order to position dental sample at an appropriate height. Dental sample 820 is then affixed to sample holder 800, where a selected portion of dental sample 820 is placed near to or in contact with marker 895 (as shown in FIGS. 9(e)-(h)), such that when sample platform 880 (and the optional secondary platforms) is installed on base 810, the selected portion of dental sample 820 is at substantially co-incident, co-planar, or proximal with the scanning area. Sample platform 880, and any optionally included secondary platforms, are then removed from mounting platform 850 and installed onto the base 810 in sample chamber 440 (shown in FIG. 7), in order to allow the incident optical beam to scan the selected region of dental sample 820.

Figure 9:
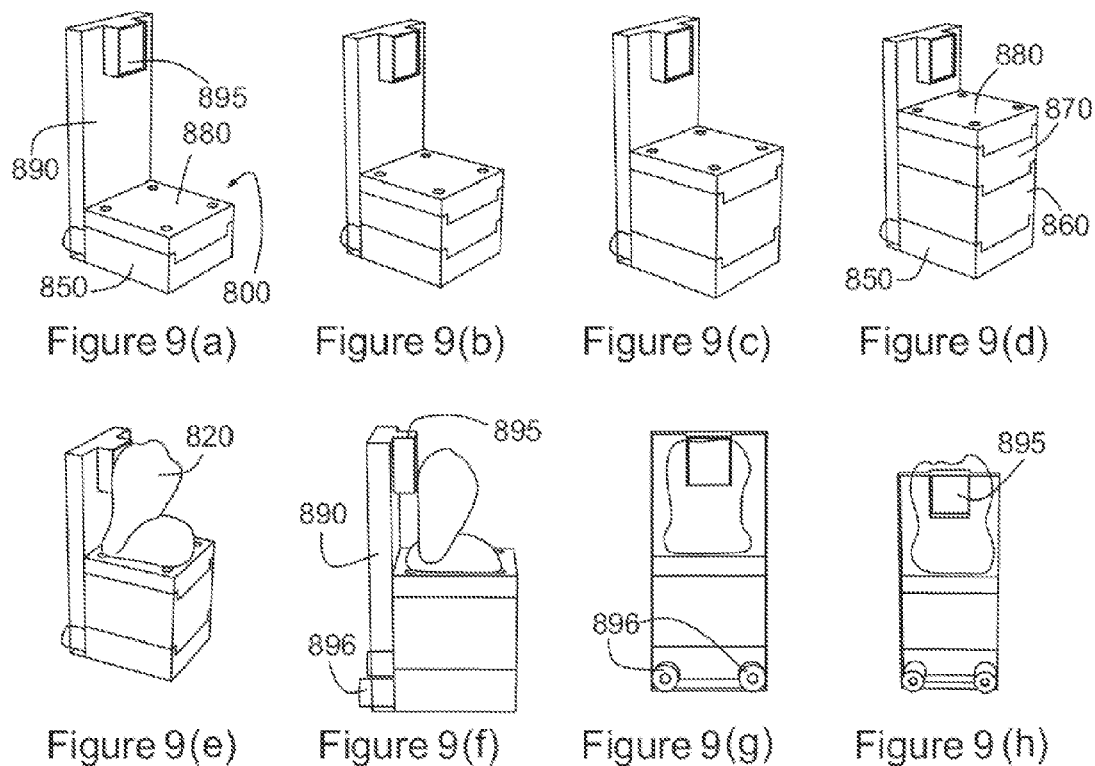
FIGS. 9(a)-(h) are photographs showing the securing of a dental sample on the example dental sample holder at a suitable height.

In one embodiment, as shown in FIGS. 9(*a*)-9(*h*), marker 895 and/or a supporting structure 890 for marker 895 may be at least partially transparent, in order to allow for the visualization of the selected portion of dental sample 820 when marker 895 is installed on dental sample holder 800. In one example implementation, marker 895 and/or supporting structure 890 may be formed from transparent polycarbonate.

In some embodiments, the system may be employed for the non-invasive and non-destructive longitudinal monitoring of a sample. In some embodiments, the system may be employed for performing in-vitro diagnostic measurements of dental samples. Advantageously, the system need not be re-calibrated when the sample holder is removed and replaced. For example, in some embodiments, the sample holder may be removed between subsequent measurements in order to apply a treatment, therapy, and/or induced degradation or pathology to the dental sample, and the system may be employed to monitor the long term status of the dental sample. The lack of a need to recalibrate the system (i.e. the relative position between the dental sample and the measurement region) between measurements avoids the need to calibrate the sample position for each measurement, a process that can be both time consuming and error prone.

Example uses of the system include the measurement and/or monitoring of ongoing demineralization and/or remineralization, white spot lesions, brown spot lesions, longitudinal studies to assess the efficacy of remineralization and/or demineralization agents, erosion studies, caries around dental restorations, and the non-destructive imaging of in-situ treated samples.

In one example implementation, the system may be employed to monitor the effect of a treatment protocol on one or more carious lesions in a dental sample, where successive measurements are made over time, in between treatment steps. Due to the fixed calibration of the sample relative to the system, demineralization and remineralization studies may be performed using the same sample, reducing the influence of inter-sample biological variability.

In some embodiments, the system may be employed for the detection and monitoring of small areas of decay, for example, as small as 50 microns in size. The decay may be present, for example, on smooth enamel, or, as erosive lesions caused by exposure to acidic liquids.

Embodiments of the present in-vitro dental detection system may be useful in a wide range of applications due to the non-destructive nature of the analysis, the ability to obtain images with ability to specify measurement resolution, the ability to monitor treatment efficacy in a sample as a function of time, and the ability to assess uniformity of investigated sample. In embodiments that employ photothermal radiometry and luminescence detection, the system may be employed to compare to a sample to normal healthy enamel or other mineralized tissue, and thereby assess the health of the in-vitro sample and monitor ongoing changes.

The following examples are presented to enable those skilled in the art to understand and to practice embodiments of the present disclosure. They should not be considered as a limitation on the scope of the present embodiments, but merely as being illustrative and representative thereof. In the Examples below, the example implementation shown in FIGS. 2 to 9 is henceforth referred to as the "Canary Lab System™".

EXAMPLES

Example 1

Photothermal and Luminescence Detection of Dental Caries

In a photothermal radiation or photothermal radiation-luminescence system, such as The Canary System™, a beam of energy (typically a laser) intensity-modulated at a certain frequency is focused onto the sample surface. The resulting periodic heat flow due to the absorbed optical energy in the material is a diffusive process, producing a periodic temperature rise (distribution) which is called a "thermal wave". This temperature distribution in turn causes a modulated thermal infrared (black-body or Planck radiation) emission which is used to monitor the material under examination. Photothermal radiation has the ability to penetrate, and yield information about, an opaque medium well beyond the range of optical imaging. Specifically, the frequency dependence of the penetration depth of thermal waves makes it possible to perform depth profiling of materials.

In photothermal radiation applications involving turbid media, such as hard dental tissue, depth information is obtained following optical-to-thermal energy conversion and transport of the incident laser power in two distinct modes: conductively, from a near-surface distance controlled by the thermal diffusivity of enamel (50-500 μm) [Brown W S, Dewey W A, Jacobs H R: Thermal properties of teeth. J Dent Res 1970; 49: 752-754] and radiatively, through blackbody emissions from considerably deeper regions commensurate with the optical penetration of the diffusely scattered laser-induced optical field (several mm). For example, deeper subsurface lesions are possible by using a longer wavelength (830-nm) laser source than a 659-nm probe [Jeon, R. J., Han, C., Mandelis, A., Sanchez, V., Abrams, S. H., "Non-intrusive, Non-contacting Frequency-Domain Photothermal Radiometry and Luminescence Depth Profilometry of Carious and Artificial Subsurface Lesions in Human Teeth," Journal of Biomedical Optics 2004, July-August, 9, #4, 809-819].

Photothermal radiation measurements of artificially induced caries on human teeth have shown that the photothermal radiation amplitude increases gradually with increasing demineralization time and decreases after remineralization. The photothermal radiation phase also shows gradual and consistent changes with demineralization and demineralization treatment. This behaviour has been attributed to the higher scatter of the diffuse photon field and to thermal-wave confinement in the form of standing waves in the treated region, accompanied by decreased thermophysical properties (thermal diffusivity and thermal conductivity).

Good correlation of photothermal radiation-luminescence results with the mineral loss or the lesion depth measured with TMR results has indicated that photothermal radiation-luminescence is capable of monitoring artificially created carious lesions, their evolution during demineralization, and the reversal of the lesions under the growth of a remineralized surface layer [Jeon R. J., Hellen A., Matvienko A., Mandelis A., Abrams S. H., Amaechi B. T., In vitro Detection and Quantification of Enamel and Root Caries Using Infrared Photothermal Radiometry and Modulated Luminescence. Journal of Biomedical Optics 13(3), 048803, 2008]. The photothermal radiation-luminescence methodology for dental applications has been extensively studied. Literature reports include applications in depth profiling, early lesion evaluation, caries detection in smooth, occlusal, root and interproximal areas, and theoretical modeling.

One of the main advantages of photothermal radiation-luminescence is the ability to perform depth profiling through scanning of the excitation source modulation frequency. By selecting a fixed modulation frequency, radiometric measurements at different depths in the enamel can be obtained. The first attempt to apply the depth profilometric capability of photothermal radiation-luminescence toward the inspection of dental defects was reported by Mandelis et al. [Jeon, R. J., Mandelis, A., Abrams, S. H., "Depth profilometric case studies in caries diagnostics of human teeth using modulated laser radiometry and luminescence", Review of Scientific Instruments, 2003, January, Volume 74 #1, pages 380-383]. In these studies a laser of 488 nm was used as the excitation source. This work showed that the photothermal radiometric signals were inversely correlated with the luminescence signals, as a result of the nature of the two physical signal generation processes. While the photothermal radiation amplitude increased for carious lesions the luminescence amplitude decreased. The luminescence signal results were consistent with previous reports [R. Hibst et al.]. In addition, these studies showed that the radiometric amplitude exhibited much superior dynamic (2 orders of magnitude signal resolution) range to luminescence (a factor of 2 only) in distinguishing between intact and cracked sub-surface structures in the enamel. Furthermore, the radiometric signal (amplitude and phase) produced dental images with much better defect localization, delineation, and resolution than those obtained with modulated luminescence.

Further experimental studies [Jeon, R. J., Han, C., Mandelis, A., Sanchez, V., Abrams, S. H., "Non-intrusive, Non-contacting Frequency-Domain Photothermal Radiometry and Luminescence Depth Profilometry of Carious and Artificial Sub-surface Lesions in Human Teeth," Journal of Biomedical Optics 2004, July-August, 9, #4, 809-819] used excitation sources of 659 and 830 nm to assess the feasibility of photothermal radiation-luminescence to detect deep lesions. Photothermal radiation frequency scans over the surface of an occlusal fissure into demineralized enamel and dentin showed higher amplitude than those for healthy teeth, as well as a pronounced curvature in both the amplitude and phase signal channels. These can be excellent markers for the diagnosis of subsurface carious lesions. The results showed that photothermal radiation-luminescence is able to detect artificial subsurface defects with sharp boundaries at depths greater than 5 mm. In addition photothermal radiation exhibited superior sensitivity to the presence of sharp boundaries, as well as to changes in natural demineralized regions of the tooth. These results suggested the possibility to detect carious lesions on both occlusal surfaces and the interproximal area of the tooth [Jeon et al.].

In experimental studies, it was found that photothermal radiation Amplitude had a very strong correlation with lesion size and shape. Luminescence phase provided limited information. Photothermal radiation Phase provided an indication of operator movement if there was a strong shift in the phase number from the norm. If this occurred, the operator was instructed to re-measure the area.

In one embodiment, in which a single unified quantitative indication of oral health is provided based on a measurement at a given location, the data from each location is stored as four separate signals; photothermal radiation amplitude and phase and luminescence amplitude and phase. A unified measure is obtained according to the following weighting formula:

photothermal radiation Amplitude weighted at 45% of the total value
photothermal radiation Phase weighted at 15% of the total value
luminescence Phase weighted at 10% of the total value
luminescence Amplitude weighted at 30% of the total value The four readings are compared to the readings one finds from the healthy enamel surface and/or from a standardized piece of hydroxyapatite. The measured signal number is compared to healthy enamel surface as well. Preferably, results from the comparison step are provided on a fixed scale for each reading, for example, on a scale of 1 to 100 (the scales need not be equal for each reading type), indicating a severity of a condition. The four fixed-scale results are then weighted as described above, providing the operator a ranking or range (for example, on a scale from 1-100) indicating the health of the area examined. The utility of multiple readings in diagnostic assessment with a photothermal radiation and luminescence detection device was illustrated in Jeon [Jeon et al., "Diagnosis of Pit and Fissure Caries Using Frequency-Domain Infrared Photothermal Radiometry and Modulated Laser Luminescence", Caries. Res. 38, 497-513, 2004].

In another embodiment, the reading from a single frequency is combined in the following manner: (photothermal radiation amplitude×photothermal radiation Phase)/(luminescence Amplitude×luminescence Phase) to create one single reading. This metric is henceforth referred to as the "Canary Number". Error checking may be performed by combining the standard deviation from each reading into one number as follows:

Luminescence Amplitude×Luminescence Phase× Photothermal Radiation Amplitude×Photothermal Radiation Phase.

The ratio of single reading/combined standard deviation is examined and if the ratio increases dramatically this indicates an error in the reading and this is conveyed to the operator. The single reading is then conveyed to the operator along with its difference from the single reading derived from examining health enamel and healthy teeth.

Example 2

Imaging of Various Dental Samples

Figure 10A:
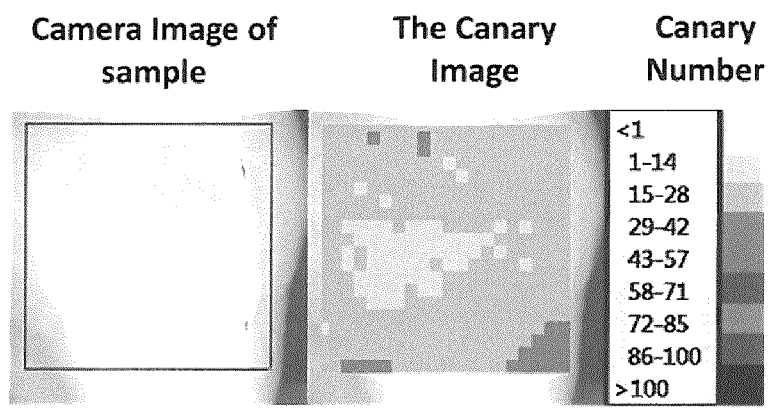
FIGS. 10(a), 10(b) and 10(c) show Canary Lab images of a dental sample having a sound enamel surface, where (a) shows the Canary Image and (b) shows the Canary Lab Image with contrast enhancement, and (c) shows the amplitude and phase components of the Canary Lab images with (with and without contrast enhancement).

FIG. 10(a) depicts a 6 mm×6 mm digital camera image (Left) and corresponding Canary image (right) of the same tooth sample exhibiting sound enamel. Both images were generated by The Canary Lab System.

A Canary image is taken within the square on the camera image, called the region-of-interest. Each pixel represents a Canary Lab scan measurement using PTR-LUM. Measurements were performed every 250 µm on the sample to generate Canary Numbers for each measured spot. The result is a composite image, The Canary Image. Corresponding legend with a scale is provided. The lower Canary Number indicates a sound tooth surface.

As shown in the Figures, the Canary Lab System image produces excellent contrast between the measured white spot lesion and the surrounding bulk sound enamel. The dark pixels in the Canary image within the white spot lesion represent the deepest areas of the incipient lesion.

As a feature of The Canary Lab System, the user can improve the spatial resolution of The Canary Image by performing measurements at smaller increments (i.e. measurements every 200 µm).

Raw Canary Images that are produced following a measurement can be edited using The Canary Software-Image Enhancement Tool, in order to enhance the contrast of the measured region of interest, as noted above. This produces the 'Canary Lab Image' shown in FIG. 10(b). The contrast enhanced Canary Lab Image identifies the most advanced (darkest) areas of the lesion from the more incipient (light) area.

Figure 10B:
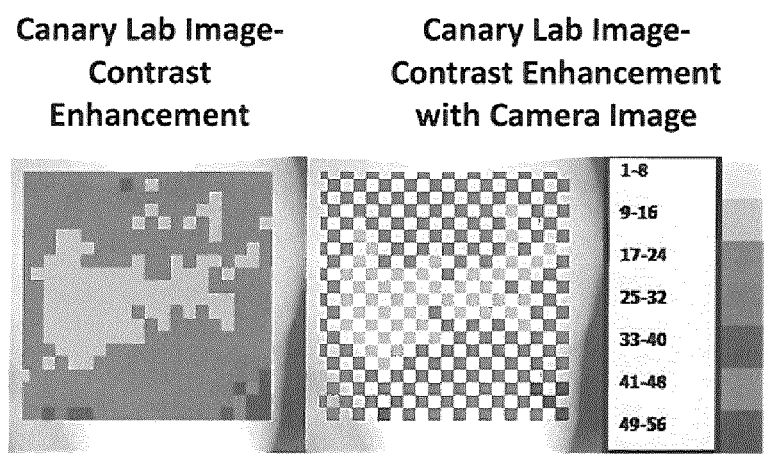
Figure 10C:
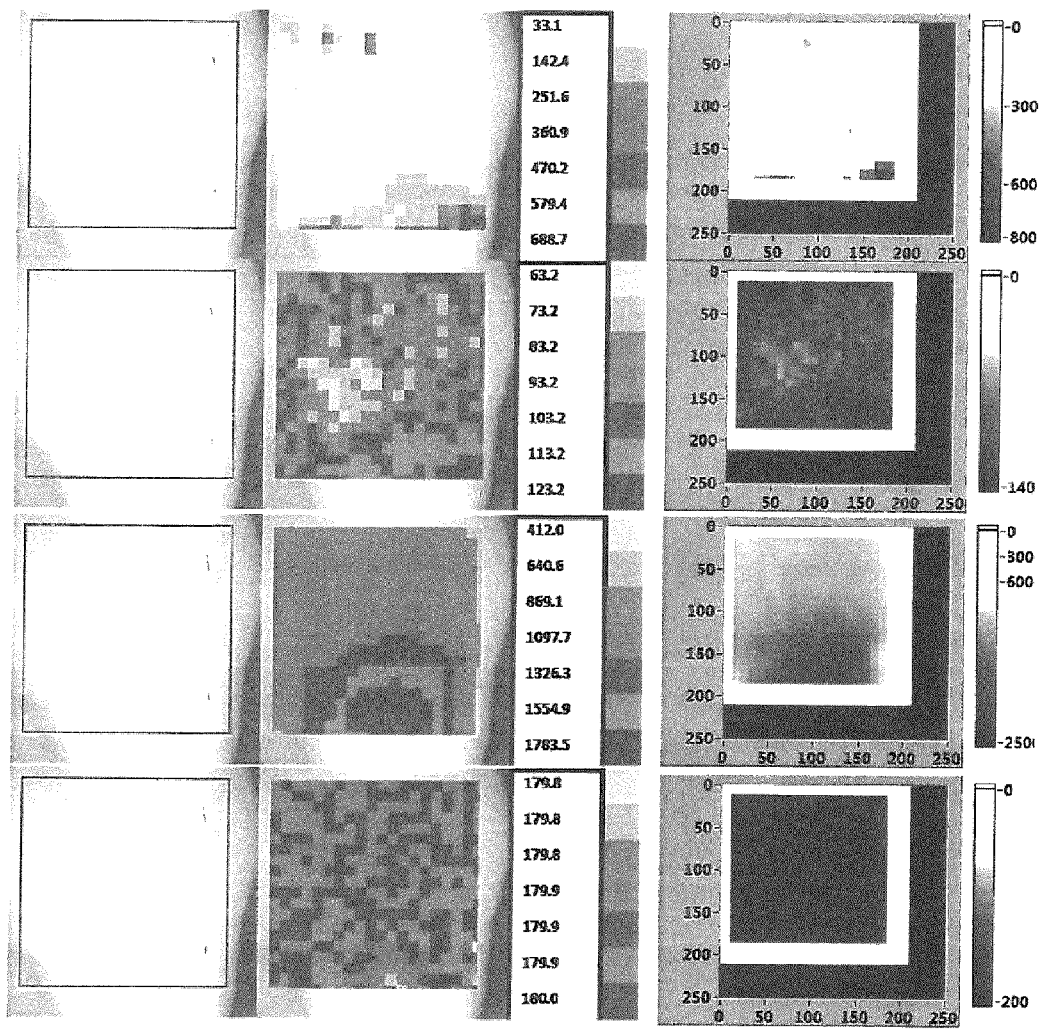

FIG. 10(c) shows the amplitude and phase components that were employed to form the images shown in FIGS. 10(a) and 10(b). The first column of images shows camera images of the sample. The second column of images shows the Canary Image, and the third column of images shows the contrast-enhanced Canary Image. The four images in the first column are identical, while the images in the second and third columns are as follows: the first row shows the PTR amplitude, the second row shows the PTR phase, the third row shows the LUM amplitude, while the fourth row shows the LUM phase.

Figure 11A:
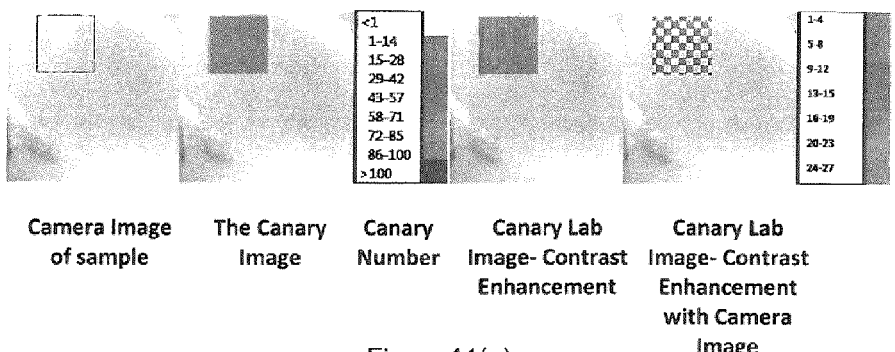
FIGS. 11(a) and 11(b) show Canary and Canary Lab images of a dental sample exhibiting an incipient white spot.
Figure 11B:
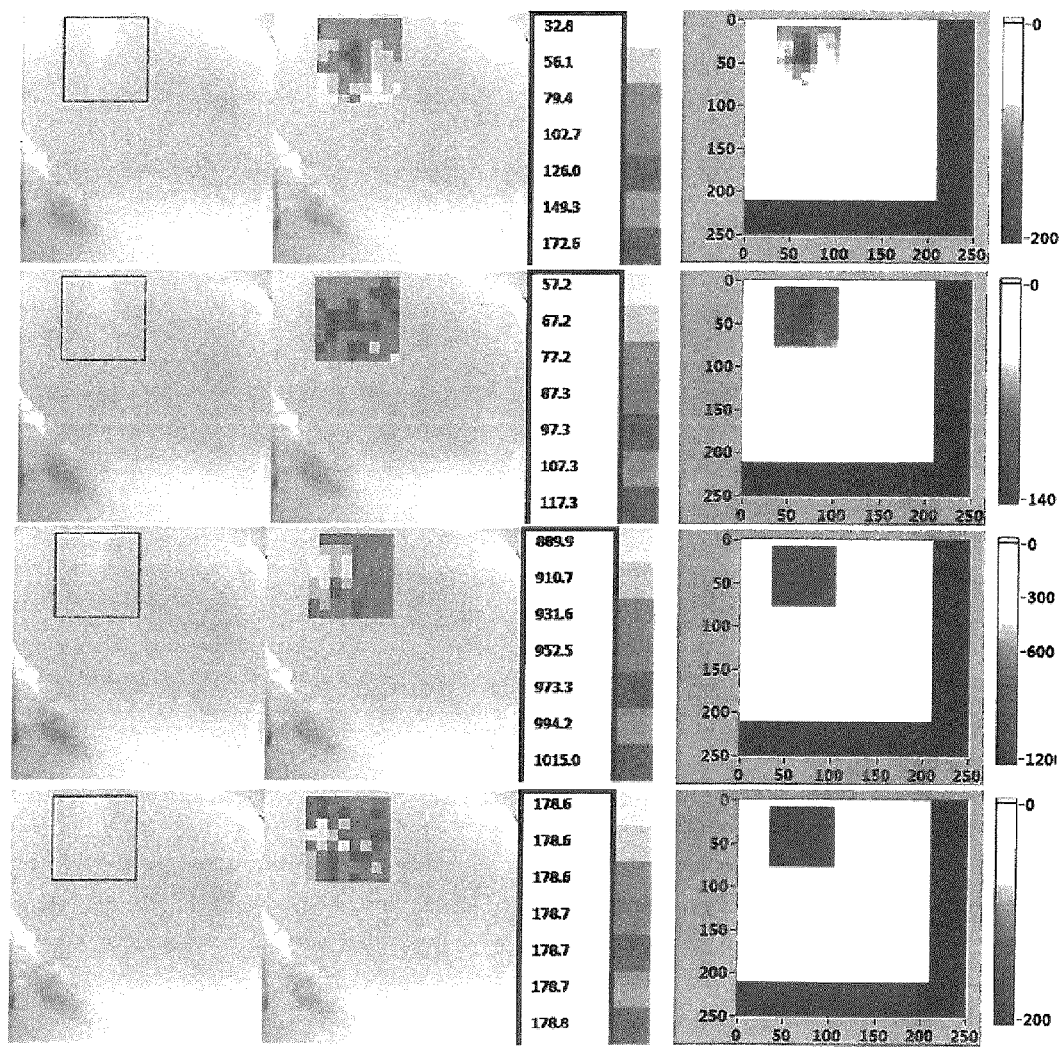
Figure 12:
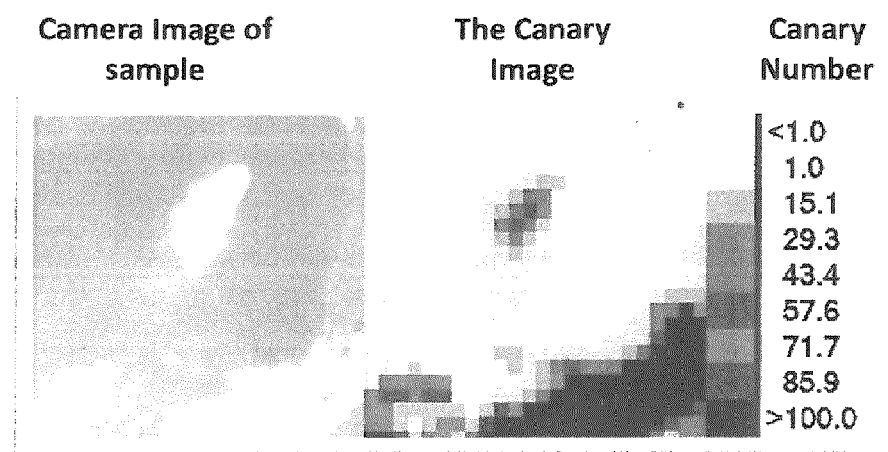
FIG. 12 shows Canary and Canary Lab images of another dental sample exhibiting an incipient white spot.
Figure 13A:
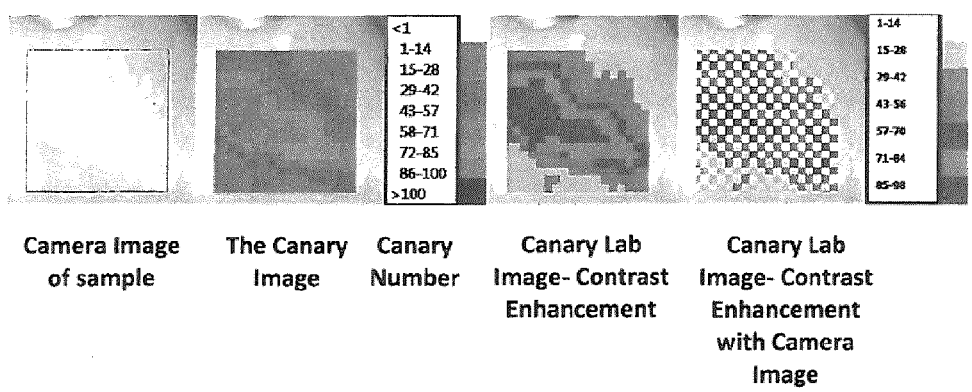
FIGS. 13(a) and (b) show Canary Lab images of dental sample exhibiting an advanced white spot lesion.
Figure 13B:
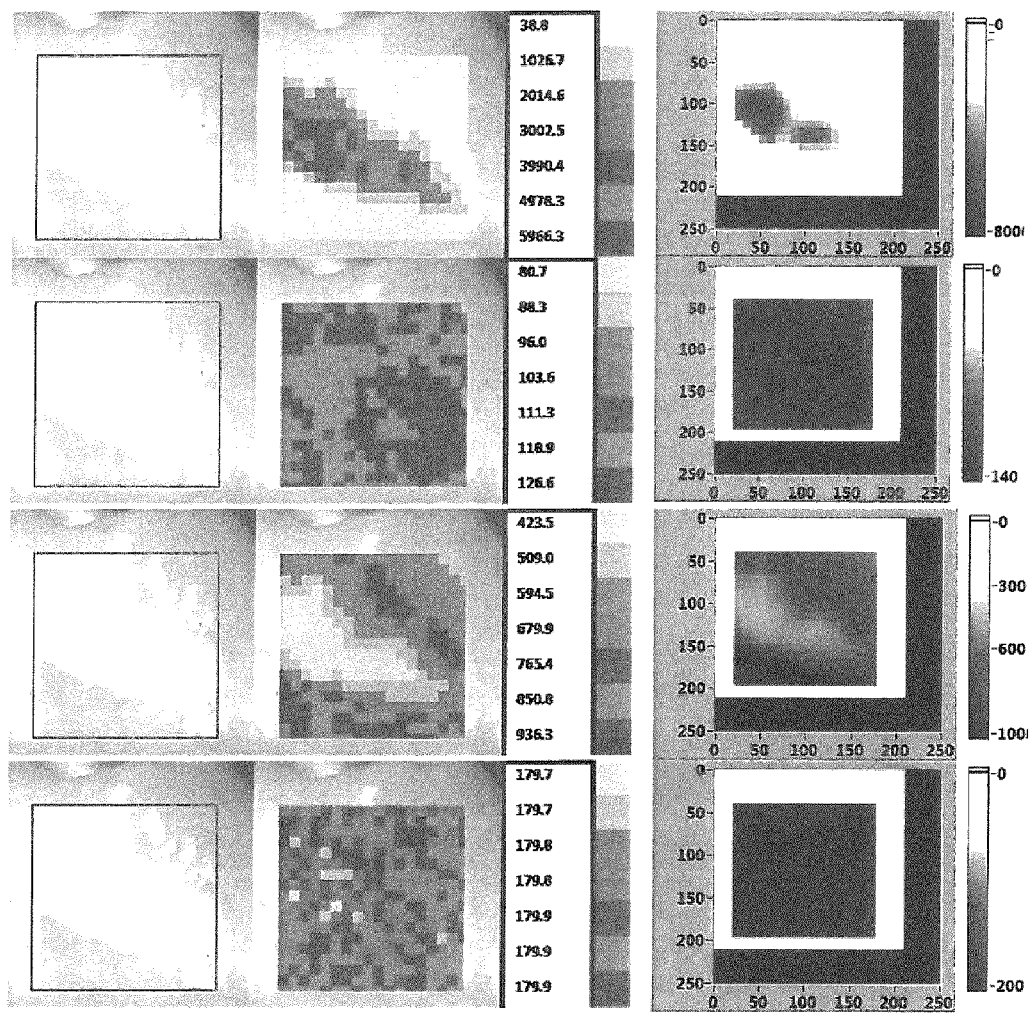

In another experiment, the Canary Lab System was employed for the imaging of a tooth exhibiting an incipient white spot. A natural incipient caries lesion was selected on an extracted tooth and mounted in the sample chamber for scanning with The Canary Lab System. Images are shown in FIGS. 11(a) and 11(b), where FIG. 11(a) shows the Canary Image, while FIG. 11(b) shows the amplitude and phase components, in the same manner as described in FIG. 10(c). Measurements of two other dental samples exhibiting white spots and advanced white spots are shown in FIG. 12 and in FIGS. 13(a) and 13(b), respectively. FIG. 13(a) shows the Canary Image, while FIG. 13(b) shows the amplitude and phase components, in the same manner as described in FIG. 10(c).

Figure 14A:
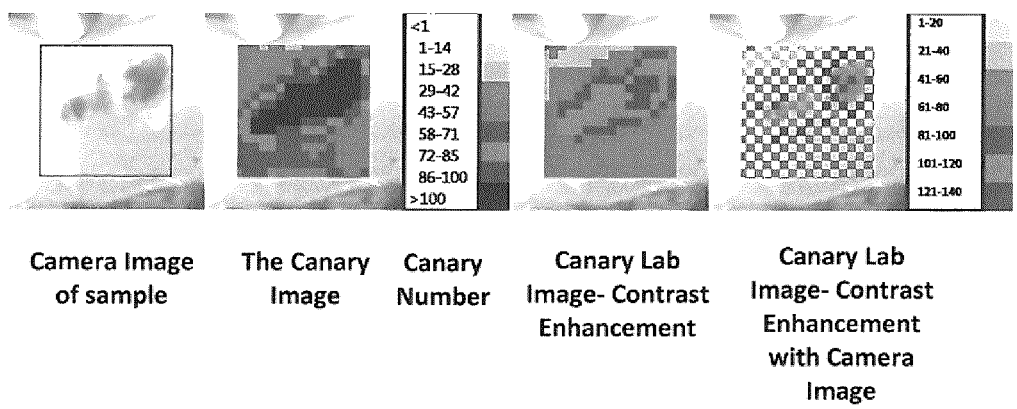
FIGS. 14(a) and (b) show Canary Lab images of dental sample exhibiting a brown spot.
Figure 14B:
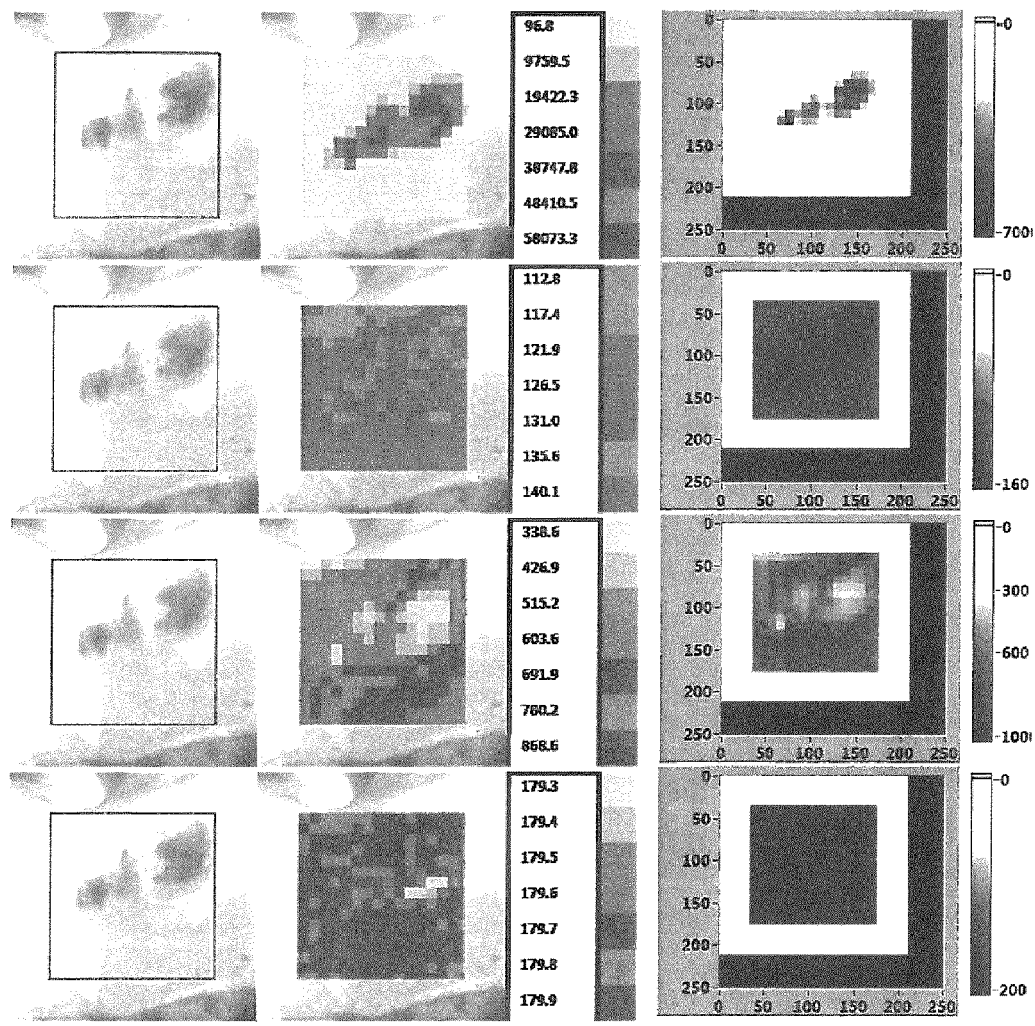
FIG. 14(b) shows the amplitude and phase components of the Canary Lab images with (with and without contrast enhancement).
Figure 15A:
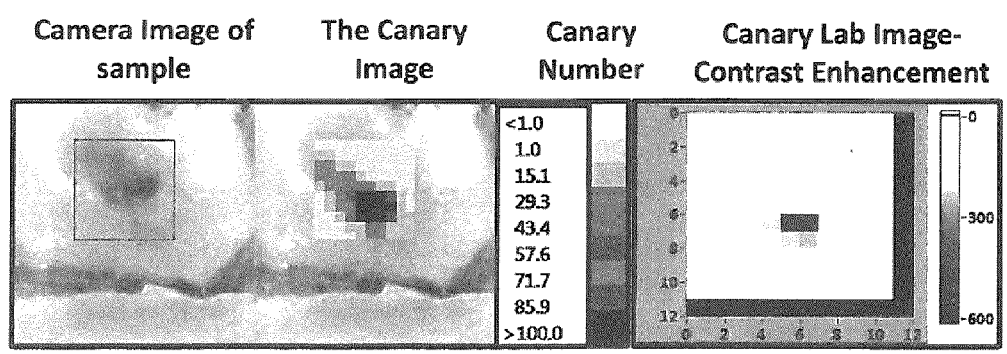
FIGS. 15(a) and (b) show Canary Lab images of another dental sample exhibiting a brown spot.
Figure 15B:
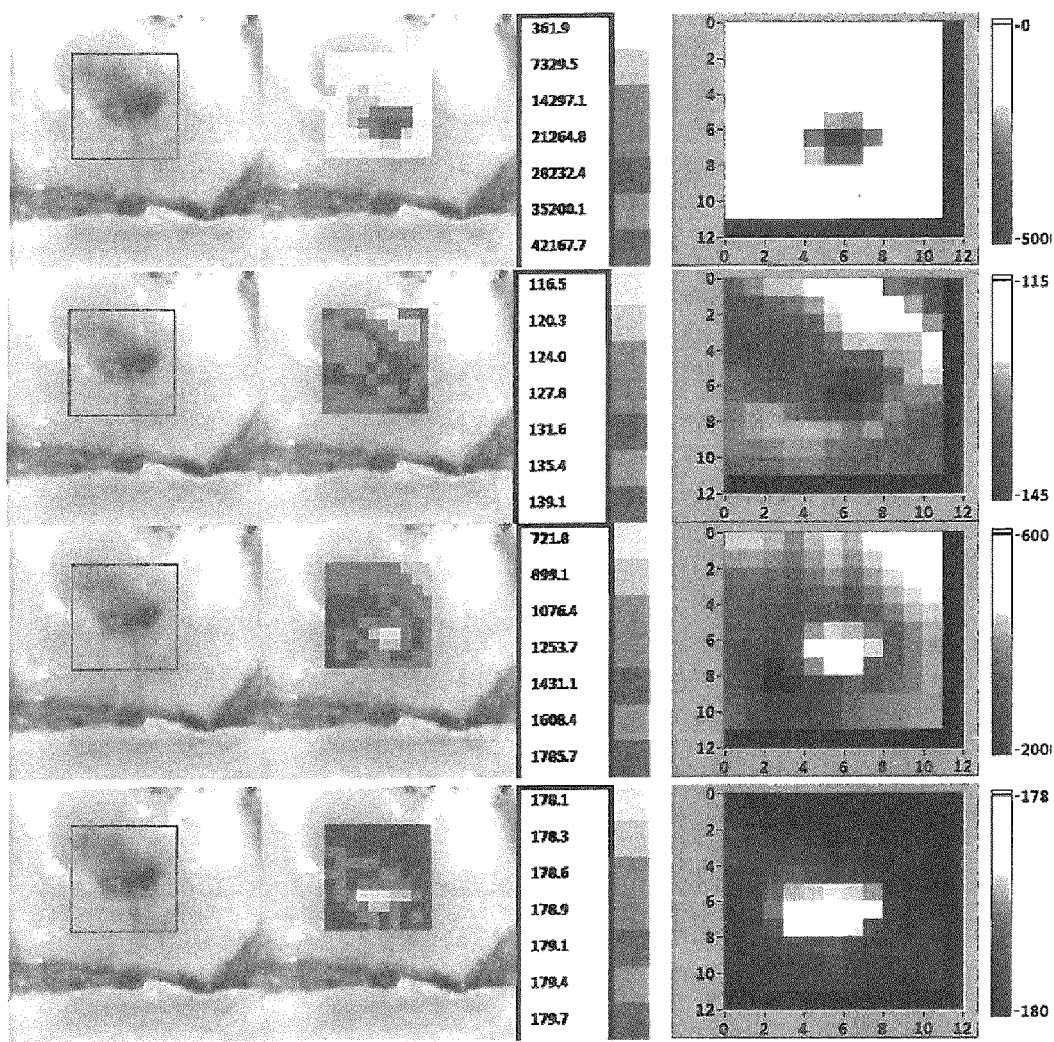
FIG. 15(b) shows the amplitude and phase components of the Canary Lab images with (with and without contrast enhancement).

The Canary Lab System was also employed for the imaging of a tooth exhibiting a brown spot. Images are shown in FIGS. 14(a) and 14(b). FIG. 14(a) shows the Canary Image, while FIG. 14(b) shows the amplitude and phase components, in the same manner as described in FIG. 10(c). A second dental sample exhibiting a brown spot was also imaged, as shown in FIGS. 15(a) and 15(b). Identification of the 'hot spots' or deepest, most advanced areas of the lesion can clearly be identified in both the raw Canary image and the Canary Lab Image. FIG. 15(a) shows the Canary Image, while FIG. 15(b) shows the amplitude and phase components, in the same manner as described in FIG. 10(c).

Figure 16A:
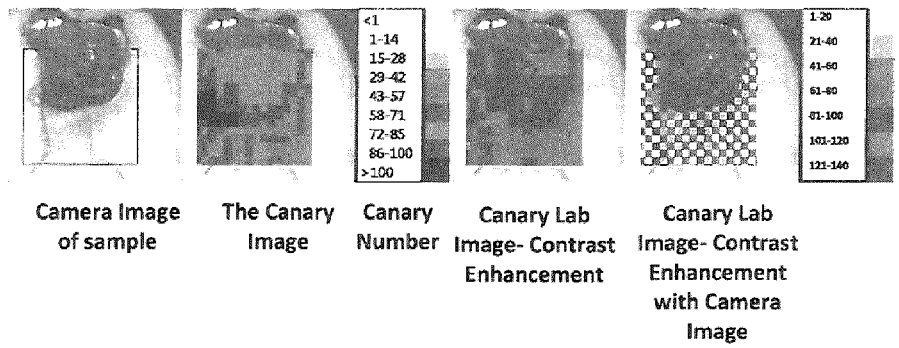
FIGS. 16(a) and (b) show Canary Lab images of dental sample having an amalgam restoration.
Figure 16B:
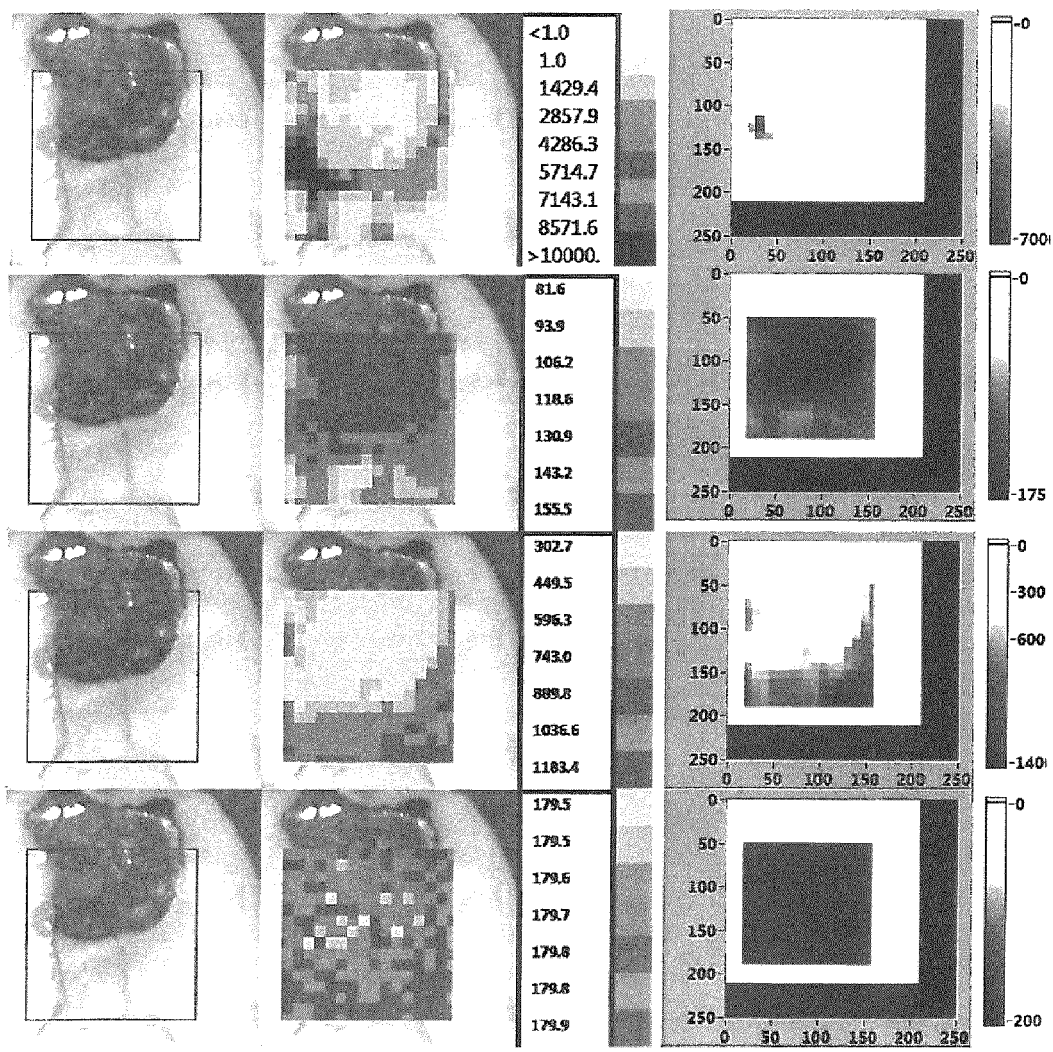
FIG. 16(b) shows the amplitude and phase components of the Canary Lab images with (with and without contrast enhancement).

FIGS. 16(a) and (b) show images generated from Canary Lab System when imaging a tooth having an amalgam restoration. FIG. 16(a) shows the Canary Image, while FIG. 16(b) shows the amplitude and phase components, in the same manner as described in FIG. 10(c).

Example 3

Sequential Etching Experiment

A sound smooth surface of an extracted tooth was selected and polished flat to remove outer enamel. The surface of interest was measured and imaged in the Canary Lab System. Subsequently, 37% phosphoric acid was used to etch a region of interest in the centre of the imaged area. The etched circle can be seen in the outlined images below. The enamel surface was etched for 5, 10 and 30 seconds with Canary Lab measurements performed after each individual etch.

Referring now to FIGS. 17(a)-(e), the microporosities generated following the 5 and 10 second etch is reflected in the Canary Lab image by the fact that the lower Canary Numbers (light grey) are replaced with higher Canary Numbers (dark grey). Following the 30 second etch the delimited etched circle can clearly be visualized with the higher Canary Numbers (darker grey). These trends are enhanced with the 60 second etch. This expected behaviour occurs as the microporosities of the etched surface confine the converted thermal energy to the defect region and as a result, emits a greater photothermal response. This occurs with a concomitant reduction in the luminescence response as the etched white surface is highly scattering of both the incident and converted light.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An apparatus for performing in-vitro measurements on a dental sample, the apparatus comprising:
a housing;
an optical detection module provided within said housing, wherein said optical detection module is configured to direct an incident optical beam over a measurement region and to detect optical radiation responsively emitted by the dental sample when at least a portion of the dental sample is positioned at or near the measurement region;
a control and processing unit provided within said housing, wherein said control and processing unit is configured to control said optical detection module and to generate an image by processing signals provided by said optical detection module in response to the detection of the optical radiation;
a sample holder for supporting the dental sample; and
an attachment mechanism provided within said housing for removably securing said sample holder in a preselected position and orientation relative to the measurement region;
wherein said attachment mechanism and said sample holder are configured such that said sample holder can be removed from the apparatus and subsequently secured by said attachment mechanism without requiring recalibration of a relative position and orientation between the dental sample and the measurement region.

2. The apparatus according to claim 1 wherein said sample holder includes a height adjustment mechanism for adjusting a difference in height between said dental sample and said measurement region.

3. The apparatus according to claim 2 wherein said sample holder further comprises a mounting device for mounting the dental sample, wherein said height adjustment mechanism is configurable for positioning said dental sample such that at least a portion of said dental sample is located at a reference location, wherein said reference location corresponds to a position of said measurement region when said sample holder is secured by said attachment mechanism.

4. The apparatus according to claim 3 wherein said mounting device includes a marker indicating said reference location.

5. The apparatus according to claim 4 wherein said marker is configured to identify a center of said measurement region.

6. The apparatus according to claim 4 wherein said mounting device comprises a mounting platform configured to receive said sample holder, wherein said marker is connected to said mounting platform.

7. The apparatus according to claim 4 wherein said marker defines a reference surface, wherein said reference surface corresponds to a location of a focal plane of said measurement region when said sample holder is secured by said attachment mechanism.

8. The apparatus according to claim 4 wherein at least a portion of said mounting device is transparent, such that said dental sample is visible through said portion of said removable mounting device for positioning at least a portion of said dental sample relative to said marker.

9. The apparatus according to claim 2 wherein said sample holder comprises a sample platform for mounting the dental sample and wherein said attachment mechanism includes a base for receiving said sample holder, and wherein said height adjustment mechanism comprises one or more platforms for insertion between said base and said sample platform, wherein said one or more platforms are removably attachable to one another and to said sample platform.

10. The apparatus according to claim 9 wherein said one or more platforms and said sample platform are configured to be magnetically attachable.

11. The apparatus according to claim 1 wherein said attachment mechanism is a magnetic attachment mechanism.

12. The apparatus according to claim 11 wherein said attachment mechanism includes a base for receiving said sample holder, and wherein said base and said sample holder each comprises one or more magnetic materials for removably secured said sample holder to said base.

13. The apparatus according to claim 12 wherein an upper portion of said base and a lower portion of said sample holder each include magnets, and wherein said magnets are oriented such that said sample holder may be removably secured to said base.

14. The apparatus according to claim 1 wherein one or more of said attachment mechanism and said sample holder include features for securing said sample holder in said pre-selected position and orientation.

15. The apparatus according to claim 1 wherein said optical detection module further comprises a scanning mechanism for scanning the incident optical beam across the dental sample over the measurement region.

16. The apparatus according to claim 15 wherein said scanning mechanism is configured to vary a position and/or orientation of said sample holder.

17. The apparatus according to claim 1 further comprising an imaging camera configured to obtain a camera image of the dental sample within the measurement region.

18. The apparatus according to claim 17 wherein said image obtained by processing signals provided by said optical detection module in response to the detection of the optical radiation is a first image and wherein said camera image is a second image, and wherein said control and processing unit is configured to co-register said first image with said second image.

19. The apparatus according to claim 17 wherein said control and processing unit is configured to produce a composite image comprising image pixels from said first image and image pixels from said second image.

20. The apparatus according to claim 19 wherein said image pixels are arranged in a checkerboard layout, such that a given image pixel from said first image has at least one image pixel from said second image located adjacent thereto.

21. The apparatus according to claim 1 wherein said control and processing unit is configured to process said image to improve the image quality of said image.

22. The apparatus according to claim 21 wherein said control and processing unit is configured to process the image for improving the contrast of the image.

* * * * *